(12) United States Patent
Goel

(10) Patent No.: US 9,668,783 B2
(45) Date of Patent: Jun. 6, 2017

(54) DEVICES AND METHOD FOR TREATMENT OF SPONDYLOTIC DISEASE

(76) Inventor: Atul Goel, Mumbai (IN)

(*) Notice: Subject to any disclaimer, the term of this patent is extended or adjusted under 35 U.S.C. 154(b) by 295 days.

(21) Appl. No.: 13/607,476

(22) Filed: Sep. 7, 2012

(65) Prior Publication Data

US 2014/0012318 A1 Jan. 9, 2014

(51) Int. Cl.
| | |
|---|---|
| *A61F 2/44* | (2006.01) |
| *A61B 17/70* | (2006.01) |
| *A61B 17/17* | (2006.01) |
| *A61F 2/46* | (2006.01) |
| *A61F 2/30* | (2006.01) |

(52) U.S. Cl.
CPC ...... *A61B 17/7064* (2013.01); *A61B 17/1757* (2013.01); *A61F 2/446* (2013.01); *A61F 2/447* (2013.01); *A61F 2/4425* (2013.01); *A61F 2/4465* (2013.01); *A61F 2/4611* (2013.01); *A61B 17/7059* (2013.01); *A61F 2/4405* (2013.01); *A61F 2002/308* (2013.01); *A61F 2002/3079* (2013.01); *A61F 2002/3085* (2013.01); *A61F 2002/30131* (2013.01); *A61F 2002/30143* (2013.01); *A61F 2002/30169* (2013.01); *A61F 2002/30172* (2013.01); *A61F 2002/30197* (2013.01); *A61F 2002/30331* (2013.01); *A61F 2002/30364* (2013.01); *A61F 2002/30578* (2013.01); *A61F 2002/30649* (2013.01); *A61F 2002/30662* (2013.01); *A61F 2002/30772* (2013.01); *A61F 2002/30774* (2013.01); *A61F 2002/30782* (2013.01); *A61F 2002/30808* (2013.01); *A61F 2002/30836* (2013.01); *A61F 2002/30841* (2013.01); *A61F 2002/30904* (2013.01); *A61F 2002/4475* (2013.01); *A61F 2002/4623* (2013.01); *A61F 2002/4627* (2013.01); *A61F 2002/4629* (2013.01)

(58) Field of Classification Search
CPC ..................................................... A61F 2/4405
USPC ........................................... 623/17.11–17.16
See application file for complete search history.

(56) References Cited

U.S. PATENT DOCUMENTS

| | | | | |
|---|---|---|---|---|
| 4,904,261 | A * | 2/1990 | Dove | A61F 2/442 623/17.16 |
| 5,702,449 | A * | 12/1997 | McKay | A61F 2/44 623/17.16 |
| 6,113,639 | A * | 9/2000 | Ray et al. | 623/17.16 |
| 6,342,074 | B1 * | 1/2002 | Simpson | A61F 2/4455 623/17.11 |
| 7,892,261 | B2 * | 2/2011 | Bonutti | A61B 17/562 606/279 |
| 8,349,011 | B2 * | 1/2013 | Foley | 623/17.11 |

(Continued)

*Primary Examiner* — David Bates
(74) *Attorney, Agent, or Firm* — MacMillan, Sobanski & Todd, LLC

(57) ABSTRACT

A device for treatment of spondylotic disease includes a distractor for distracting vertebral facets of first and second vertebrae located adjacent each other. The distractor includes a first abutment surface for interfacing with an inferior articular facet of the first vertebra. The distractor also includes a second abutment surface for interfacing with the superior articular facet of the second vertebra corresponding to the inferior articular facet of the first vertebra. The first and second abutment surfaces of the distractor engage with each other and are separated by a predetermined distance.

4 Claims, 29 Drawing Sheets

(56) References Cited

U.S. PATENT DOCUMENTS

| | | | | |
|---|---|---|---|---|
| 8,377,132 | B2* | 2/2013 | Wing | A61F 2/4465 623/17.11 |
| 8,414,651 | B2* | 4/2013 | Tyber | A61F 2/4465 623/17.15 |
| 8,608,752 | B2* | 12/2013 | Ralph et al. | 606/99 |
| 2003/0105526 | A1* | 6/2003 | Bryant | A61F 2/28 623/16.11 |
| 2005/0256578 | A1* | 11/2005 | Blatt et al. | 623/17.15 |
| 2006/0036258 | A1* | 2/2006 | Zucherman et al. | 606/90 |
| 2007/0016303 | A1* | 1/2007 | Jackson | A61B 17/7062 623/17.16 |
| 2007/0162138 | A1* | 7/2007 | Heinz | 623/17.16 |
| 2008/0071378 | A1* | 3/2008 | Zucherman et al. | 623/17.16 |
| 2009/0177203 | A1* | 7/2009 | Reiley | A61B 17/8095 606/87 |
| 2009/0177237 | A1* | 7/2009 | Zucherman et al. | 606/280 |
| 2010/0152782 | A1* | 6/2010 | Stone | A61B 17/151 606/280 |
| 2011/0040301 | A1* | 2/2011 | Blain et al. | 606/80 |
| 2011/0307061 | A1* | 12/2011 | Assell et al. | 623/17.11 |
| 2013/0035723 | A1* | 2/2013 | Donner | A61F 2/30988 606/246 |
| 2013/0123923 | A1* | 5/2013 | Pavlov | A61F 2/4455 623/17.16 |
| 2013/0131726 | A1* | 5/2013 | Suh et al. | 606/249 |

\* cited by examiner

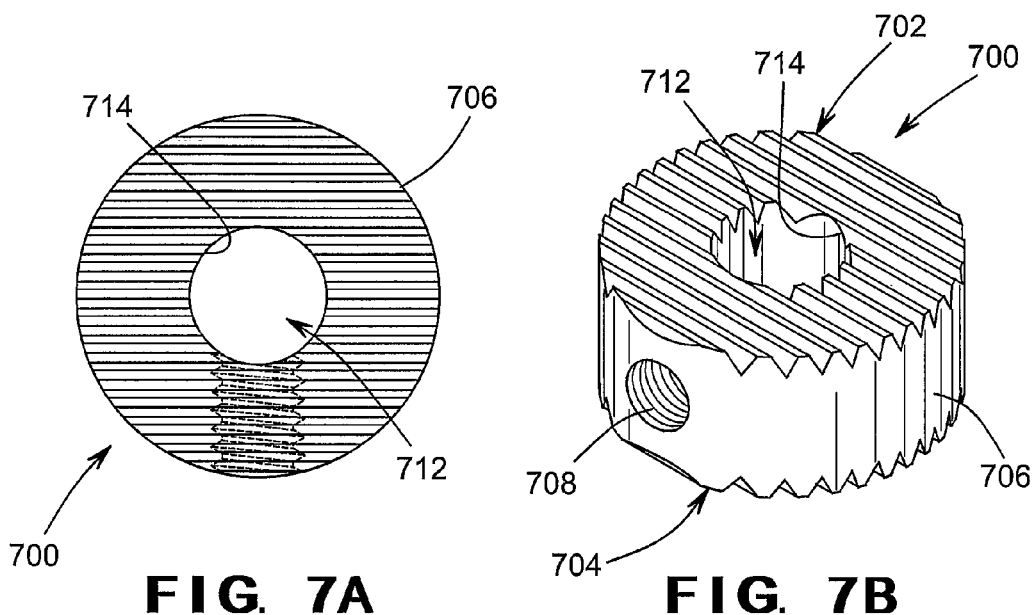
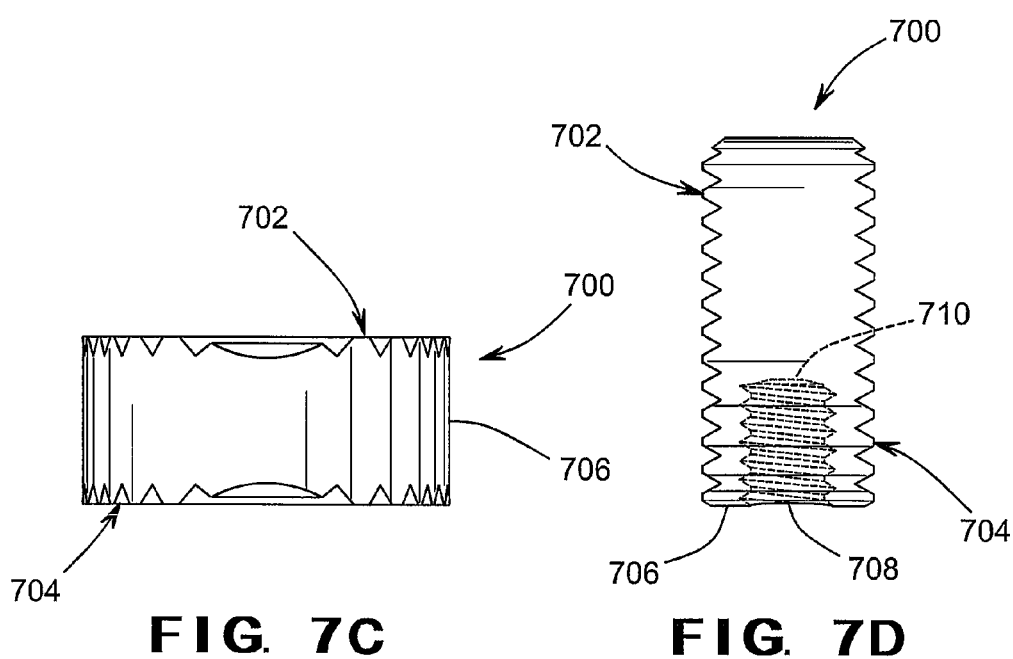

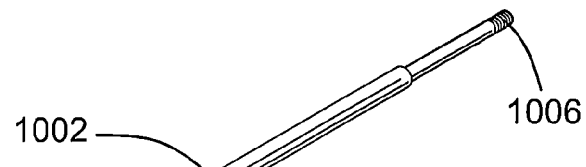
FIG. 10A
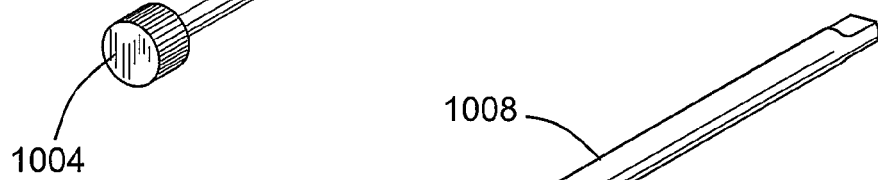
FIG. 10B
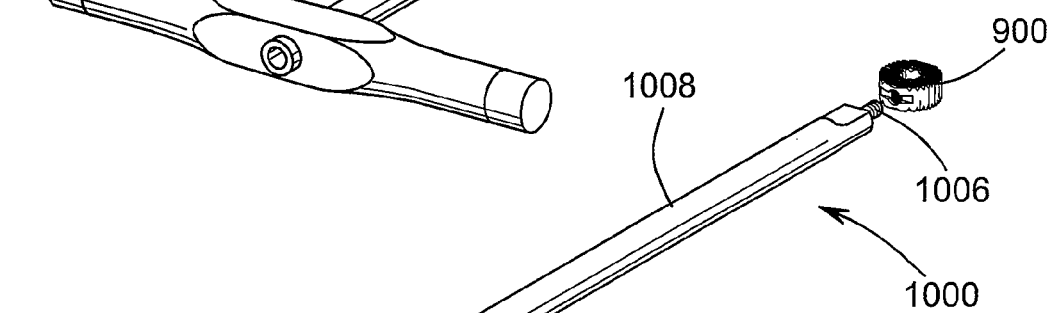
FIG. 10C
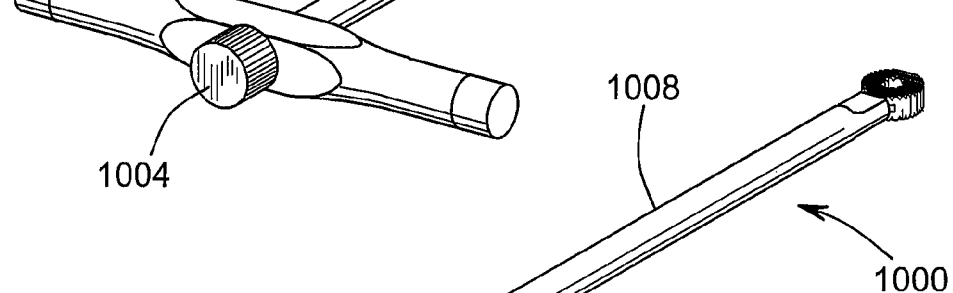
FIG. 10D
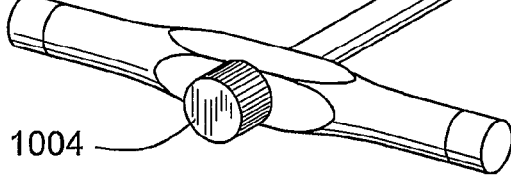

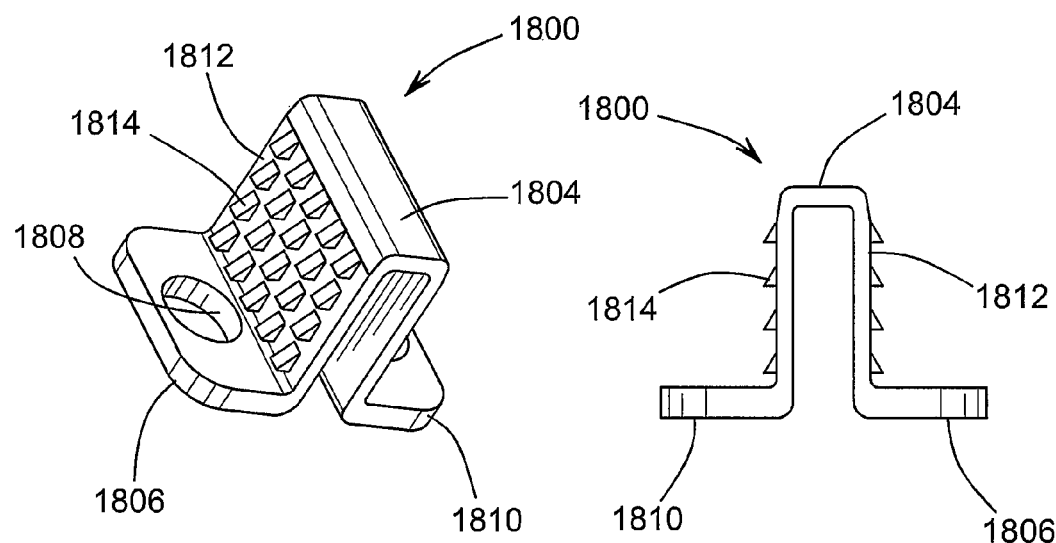
FIG. 18A   FIG. 18B
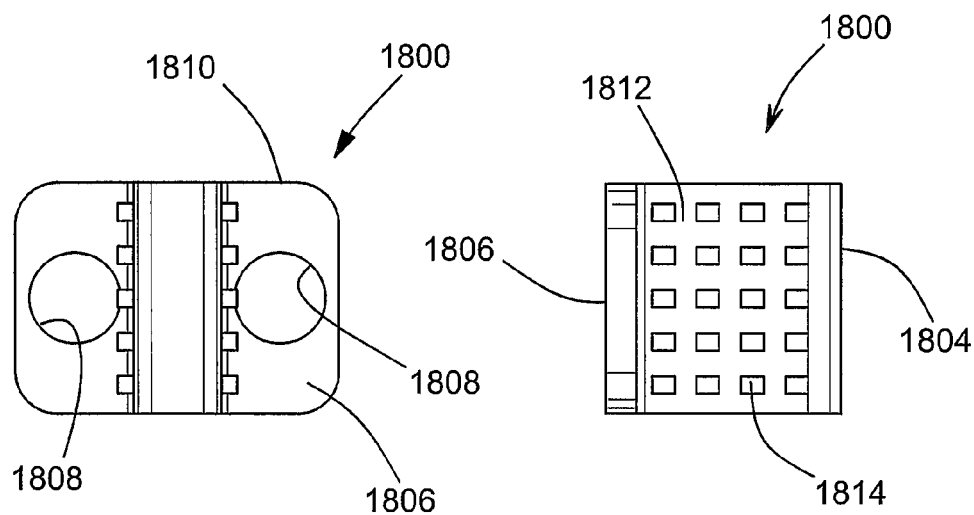
FIG. 18C   FIG. 18D

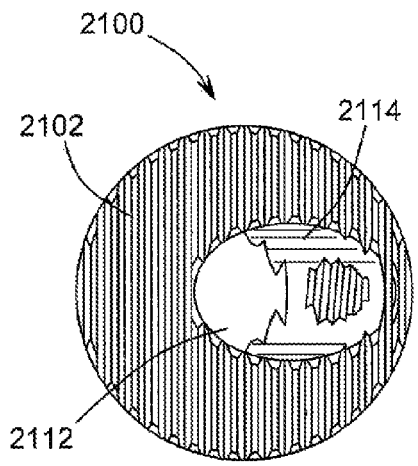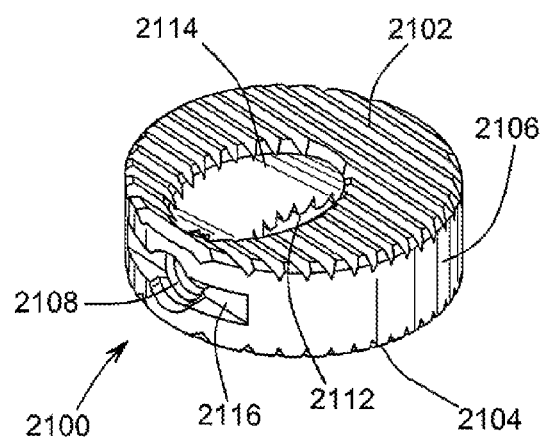
FIG. 21A    FIG. 21B
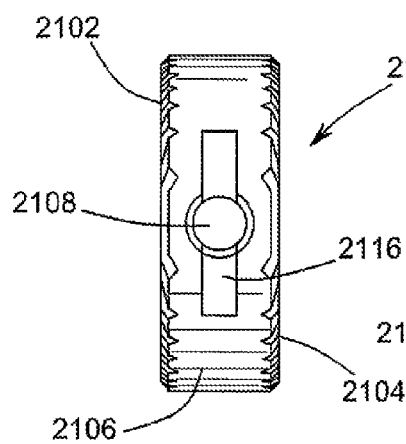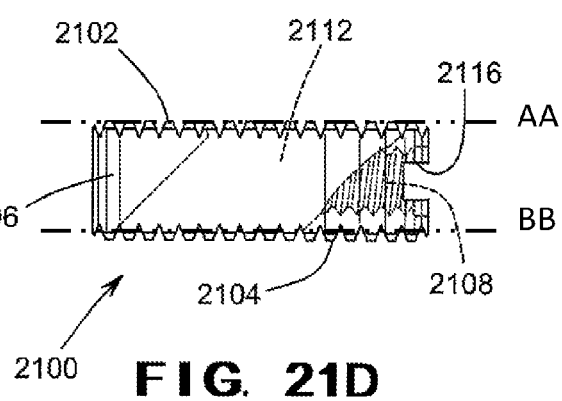
FIG. 21C    FIG. 21D

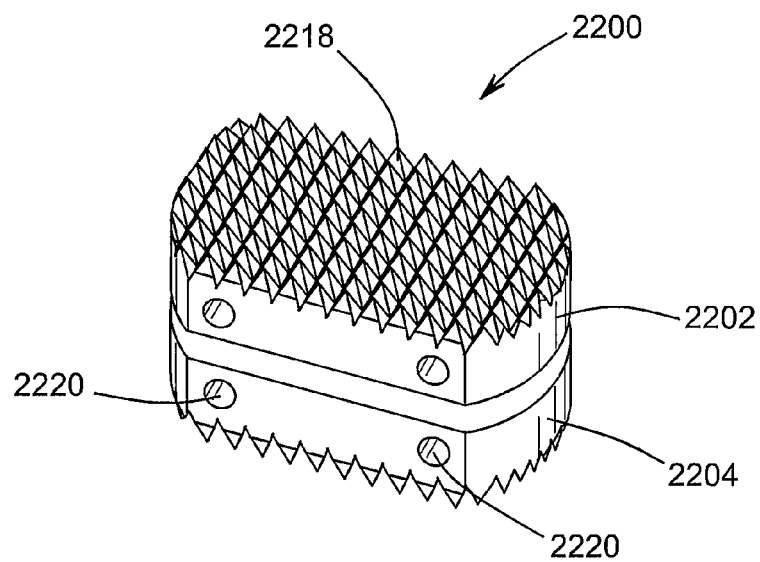
FIG. 22A
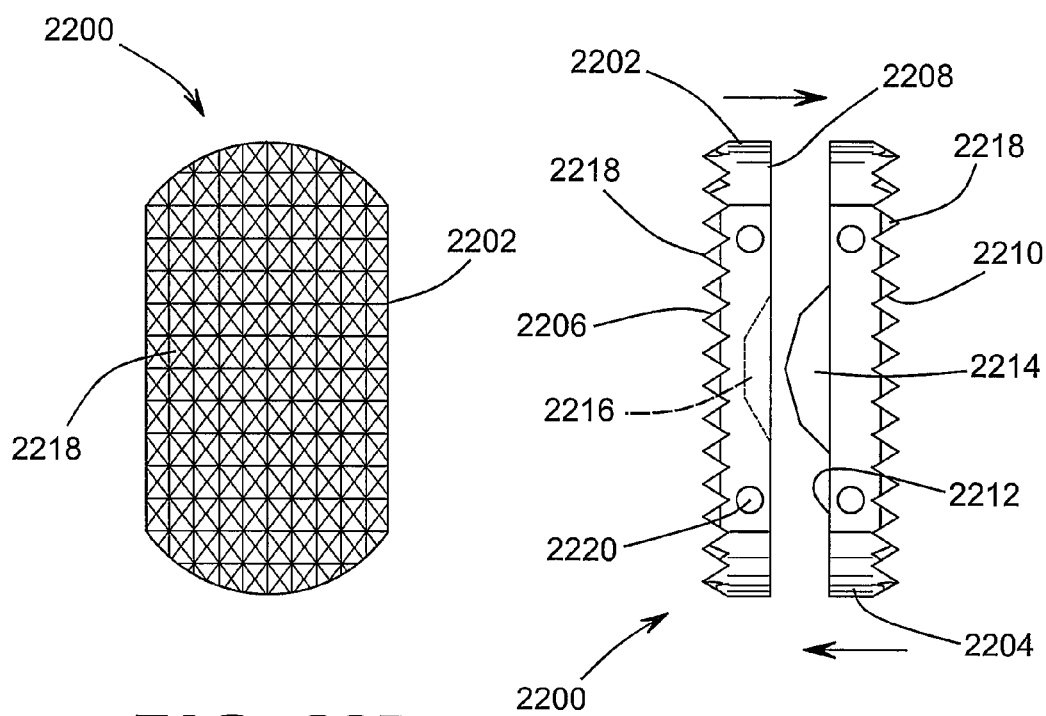
FIG. 22B  FIG. 22C

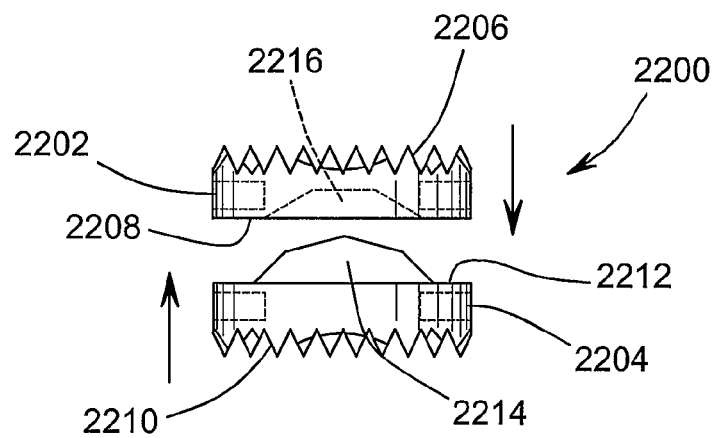
FIG. 22D
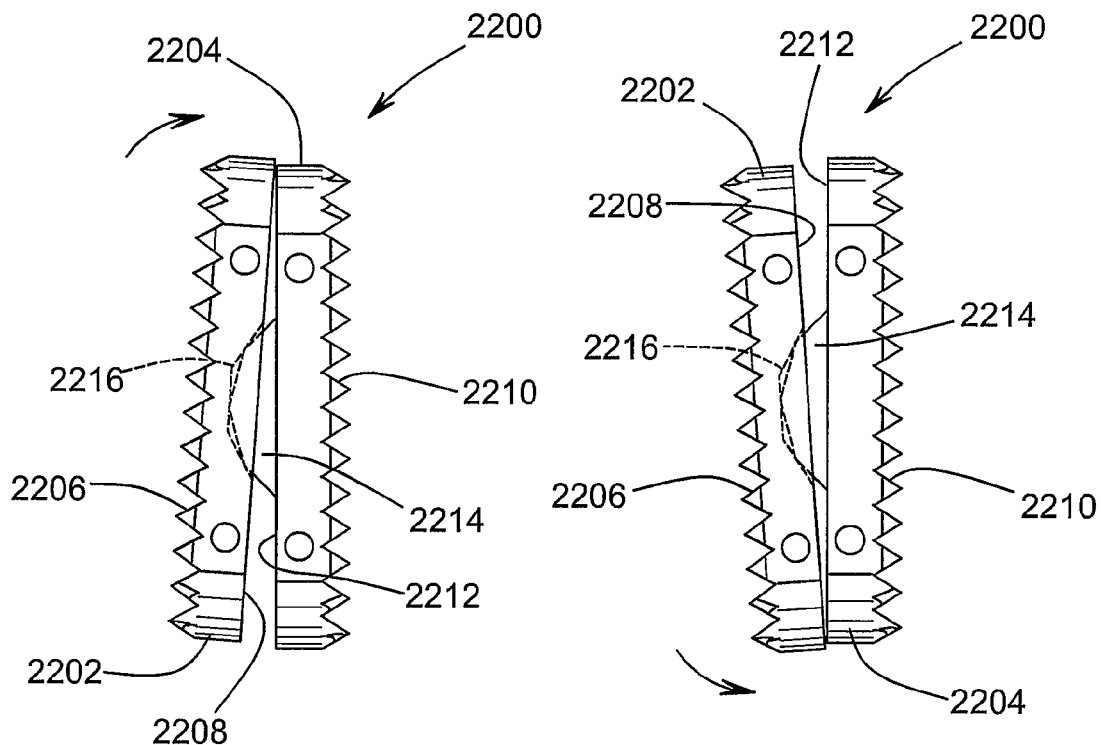
FIG. 22E  FIG. 22F

DEVICES AND METHOD FOR TREATMENT OF SPONDYLOTIC DISEASE

FIELD OF INVENTION

The present invention relates to a device and method for treatment of spondylotic disease, including single and multi-level cervical and lumbar spondylosis.

The invention has application in all cases involving reduction in the diameter of the spinal canal or root canal, prolapsed intervertebral discs, ossification of posterior longitudinal ligament and similar diseases. The inventive device can replace all previously described operations for spondylotic disease, including recently, described surgical procedures such as expansive laminoplasty, and procedures that employ inter-spinous spacers.

BACKGROUND OF THE INVENTION

Spondylotic disease or Spondylosis refers to degenerative changes in the spine that result in compression of the spinal cord or nerve roots. The process of degeneration usually begins in the old, but can also begin in young patients. It is generally known and understood that the process of degeneration begins in the cushions between the vertebrae (intervertebral discs). Degeneration is also known to involve the joints between the vertebral segments. Over time these changes cause the space between adjacent vertebrae to narrow, which may result in misalignment of adjacent vertebrae and in severe cases may lead to pressure over the nerve roots and to the spinal cord.

The patients usually present symptoms that include sensory (parasthesiae or abnormal sensations) and motor disturbances (radiculopathy—compression of the nerve root; or myelopathy—compression of spinal cord). Pain in the neck, shoulder, arm, back or leg are other common symptoms. The phenomenon can result in hand and leg weakness, gait dysfunction, loss of balance, and loss of bowel and/or bladder control.

Common treatments for spondylosis, include physiotherapy, posture and lifestyle modifications and nonsteroidal anti-inflammatory drugs. Alternative therapies such as osteopathic manipulative medicine (OMM), massage, trigger-point therapy, chiropractic care, osteopathic care and acupuncture may be utilized to control pain and maintain musculoskeletal function in some people. Surgery is occasionally performed, and typically involves removal of osteophytes (bone spurs) and/or portions of an intervertebral disc in an effort to relieve pressure on adjacent nerve roots and/or the spinal cord. Recently, some surgeons have advised distraction of the vertebral bodies and distraction of the spinous processes for fixation. Artificial disc replacement has also been advocated recently which replaces the intervertebral disc with a prosthetic implant and aims to preserve mobility of the spinal segments relative each other.

Other therapies including manual mobilization and mechanical traction of the neck and lower back have been successfully used to alleviate pain, which is reflected in their widespread application. Postural modification also frequently helps in relieving the symptoms.

Despite the solutions available in the art, when a person develops root or spinal cord compression symptoms, there is a possibility of permanent damage to the nerve root or to the cord. Under such situations surgical treatment is necessary.

There is therefore a need to develop devices and methods for addressing spondylotic disease.

SUMMARY OF THE INVENTION

An object of the invention is to provide a device and method for treatment of spondylotic disease.

The device of the present invention comprises an implant (distractor) for distracting vertebral facets of first and second vertebrae located adjacent each other. The distractor includes a first abutment surface for interfacing with an inferior articular facet of the first (rostral) vertebra and a second abutment surface for interfacing with the superior articular facet of the second (caudal) vertebra corresponding to the inferior articular facet of the first vertebra. The first and second abutment surfaces of the distractor are interconnected and separated by a predetermined distance.

The first and second abutment surfaces of the distractor may be engaged with each other by at least one rigid connector, semi-rigid connector, resilient connector or sidewall. The first and second abutment surfaces may in an embodiment be connected by a central lumen for promoting arthrodesis.

The first and second abutment surfaces of the distractor may, in an embodiment, comprise two separate plates, engaged in a manner configured to permit movement relative to each other along at least one of the x, y and z axes. In a preferred embodiment, the first and second abutment surfaces are configured to permit movement relative each other along each of the x, y and z axes.

In an embodiment, the first and second abutment surfaces of the distractor comprise an upper plate and a lower plate respectively and engage with each other by means of a ball and socket arrangement.

In another embodiment, the first and second abutment surfaces of the distractor comprise an upper plate and a lower plate respectively, and the first abutment surface is provided with a protrusion for engaging with the second abutment surface. The second abutment surface may be correspondingly provided with a recess for engaging with the protrusion. In a particular embodiment, the protrusion and recess are sized to permit relative movement between the first and second abutment surfaces.

In an embodiment of the invention the distractor is cylindrical and the first and second abutment surfaces may comprise top and bottom surfaces of the cylinder.

The distractor may have at least one recess for accommodating an impactor or holder.

The predetermined distance separating the first and second abutment surfaces may be less than or equal to the distraction sought to be achieved between the vertebral facets. In an embodiment, the predetermined distance separating the first and second abutment surfaces may be between 2 mm and 4 mm.

The distance between any two points on the perimeter of the first or second abutment surface of the distractor may in an aspect of the device, be less than or equal to 12 mm.

At least one surface of the distractor may be textured. The textured surface may comprise at least one of grooves, channels, spikes, knobs, bumps, protrusions or depressions.

The invention additionally relates to a device for implanting a vertebral facet distractor having first and second abutment surfaces engaged with each other and separated by a predetermined distance, and having a central lumen connecting the first and second abutment surfaces, wherein the central lumen is angled with respect to the first and second abutment surfaces.

The device comprises a first arm for engaging with the distractor and an angled arm affixed to the first arm. The angled arm has a first angled arm section with a first and second end, wherein the first end is affixed to the first arm. The angled arm also has a second angled arm section comprising a sleeve capable of interchangeably housing a drill or a driver. The sleeve has a first and second end, wherein the first end is affixed at an angle to the second end of the first angled arm section, such that either of the drill or driver housed within the sleeve traverses a path coincident with the angled central lumen of the distractor.

In an embodiment of the device for implanting the distractor, the first arm comprises a sleeve capable of housing a longitudinal body therewithin, for engaging with the distractor. In an embodiment, the first angled arm section and second angled arm section may be adjustably connected so as to enable variation of the angle there between. In a preferred embodiment, the angle between the first angled arm section and the second angled arm section is identical to or substantially the same as the angle of the central lumen of the distractor.

BRIEF DESCRIPTION OF THE ACCOMPANYING DRAWINGS

FIGS. 7A to 7D provide top, perspective and side views of the device of the present invention.

Figure 8A:
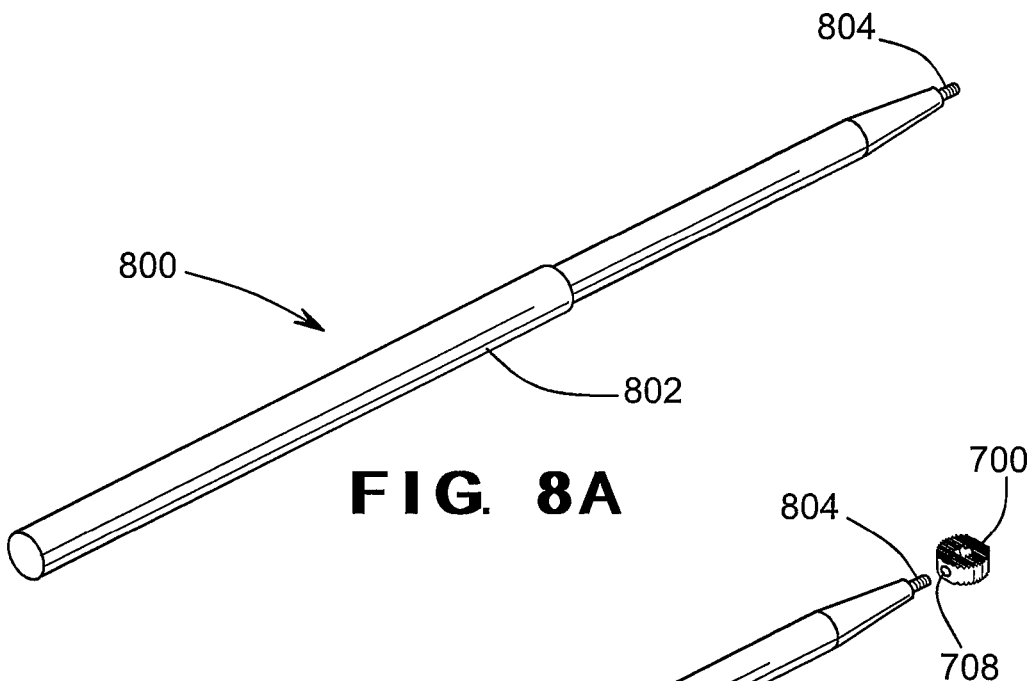
Figure 8B:
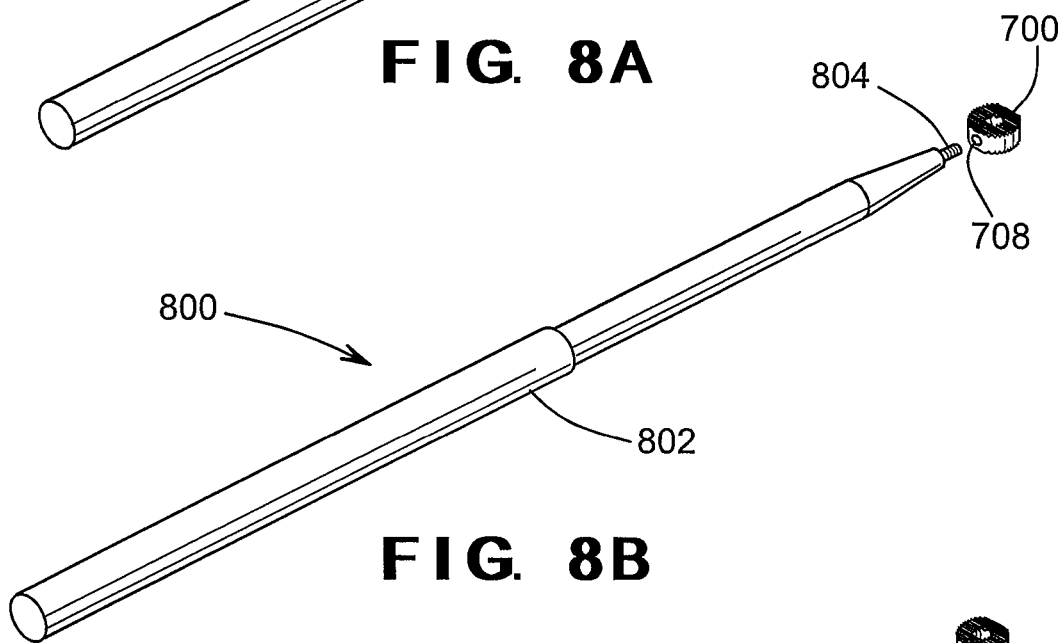
Figure 8C:
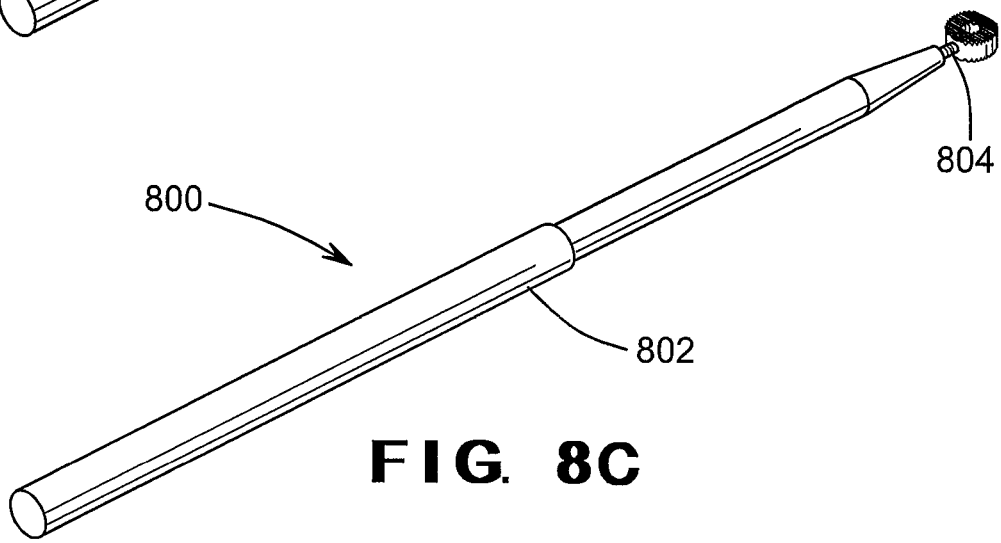

FIGS. 8A to 8C show a holder or impactor for deploying the device.

FIGS. 9A to 9D provide top, perspective and side views of an embodiment of the device having further features for promoting bone fusion.

FIGS. 10A to 10D illustrate another embodiment of a holder or impactor for deploying the device.

Figure 11A:
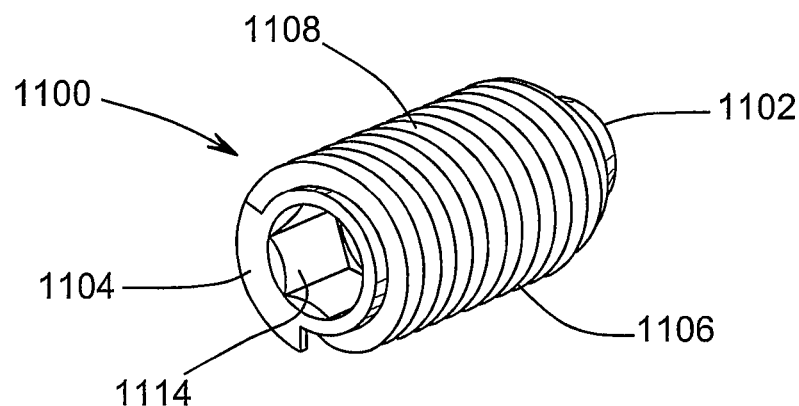
Figure 11B:
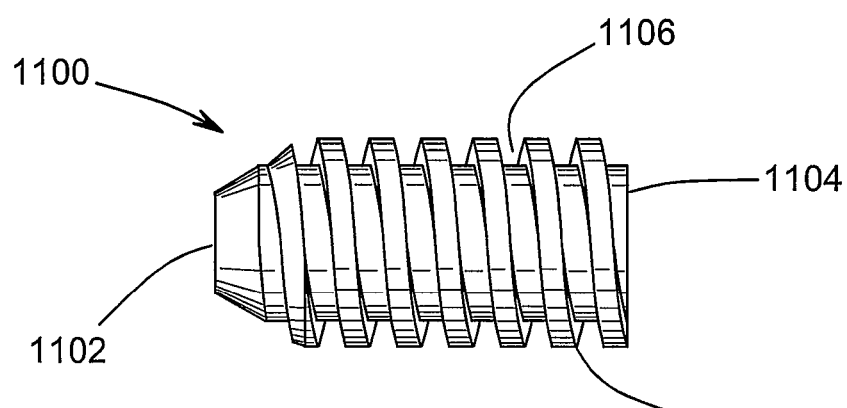
Figure 11C:
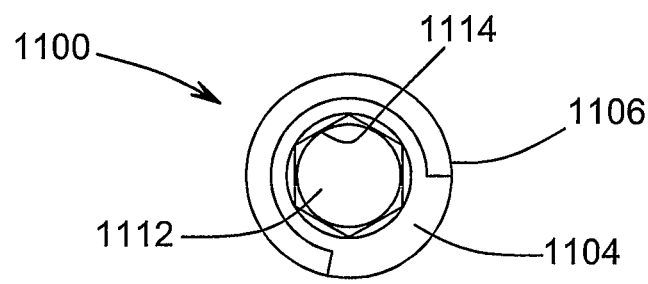

FIGS. 11A to 11C depict a threaded cylindrical embodiment of the distractor.

Figure 12A:
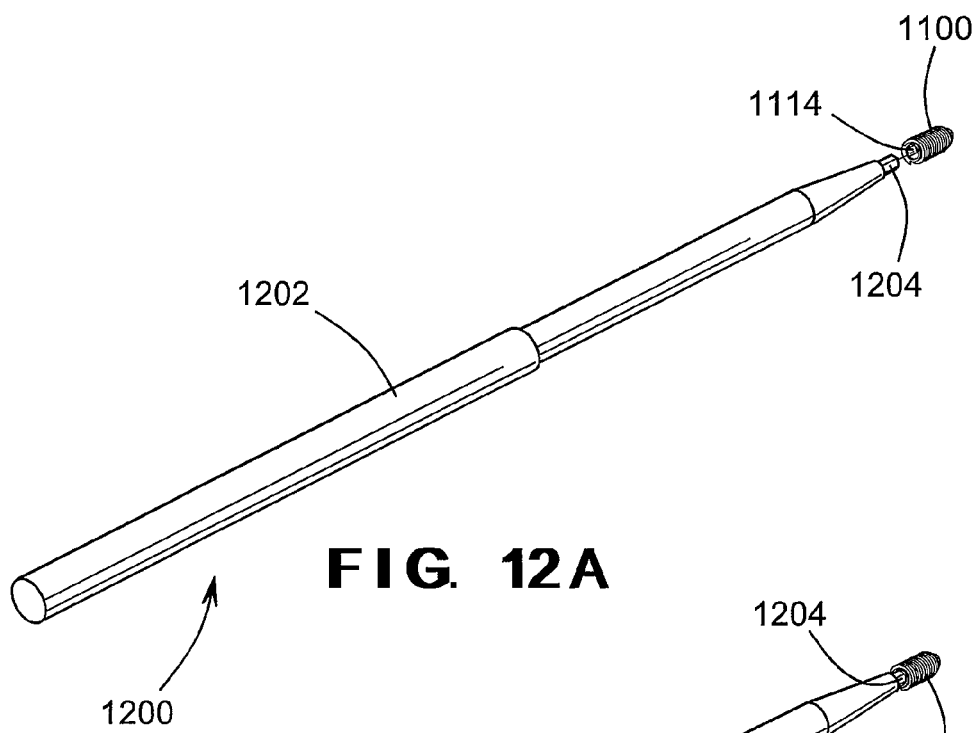
Figure 12B:
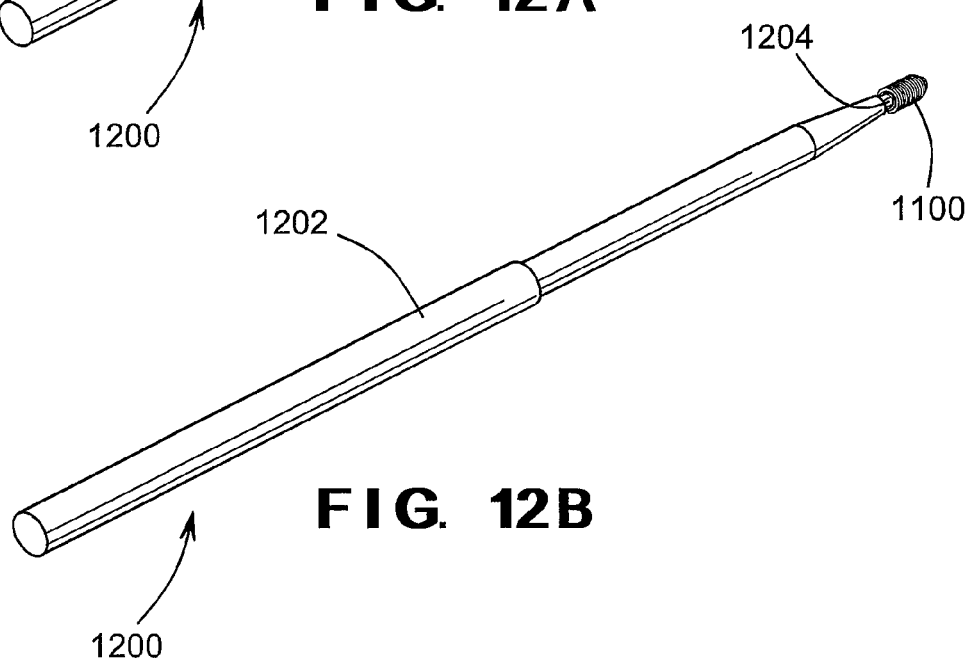
Figures 13A, 13B:
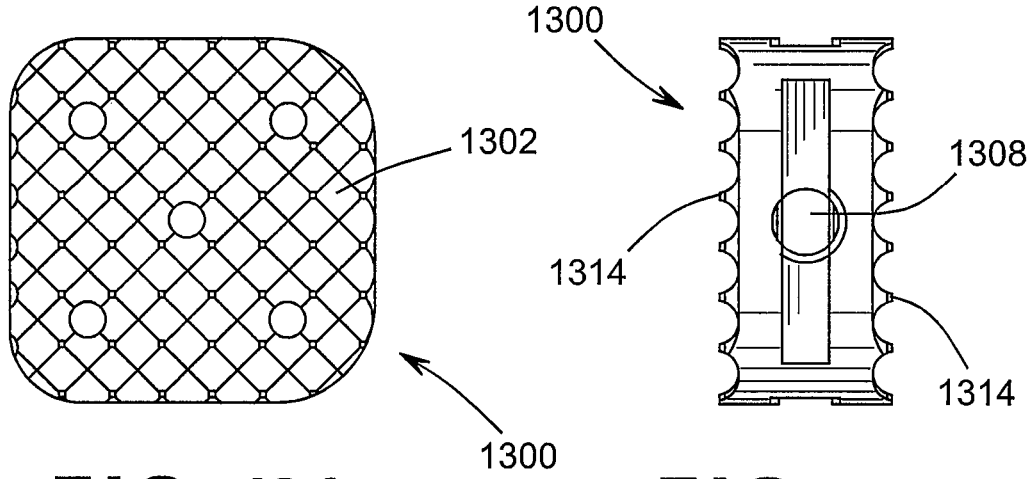
Figure 13C:
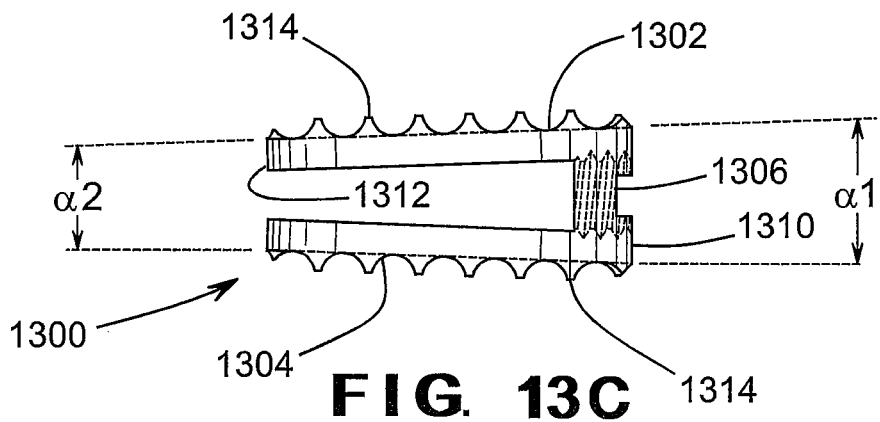
Figure 13D:
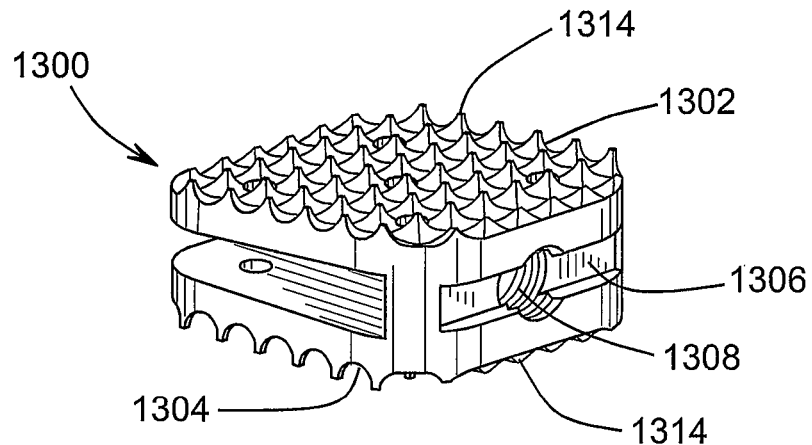

FIGS. 12A and 12B show a holder or impactor for deploying the cylindrical embodiment of the distractor.

FIGS. 13A to 13D show top, side and prespective views of an embodiment of the distractor having a tapering configuration.

Figure 14A:
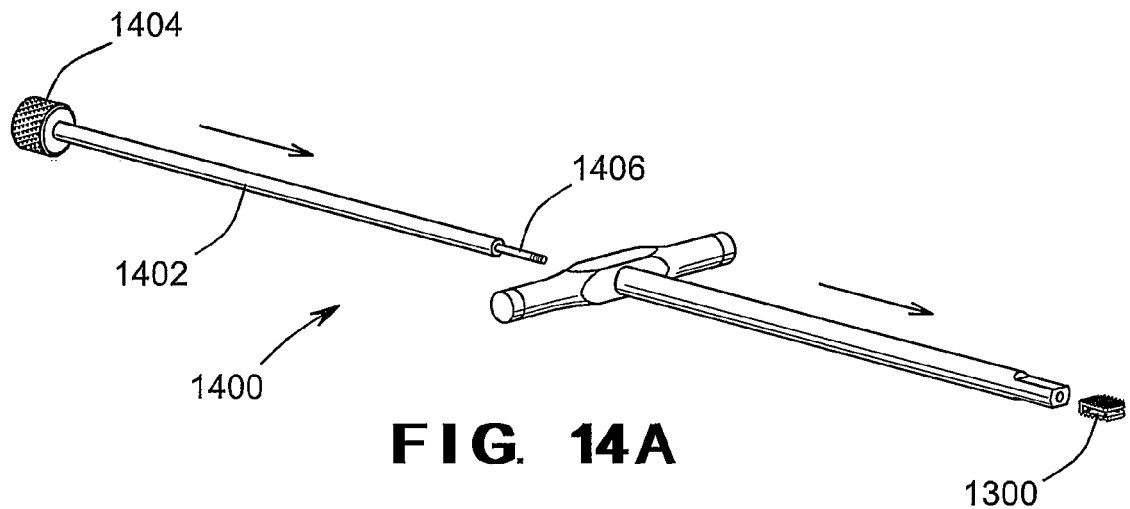
Figure 14B:
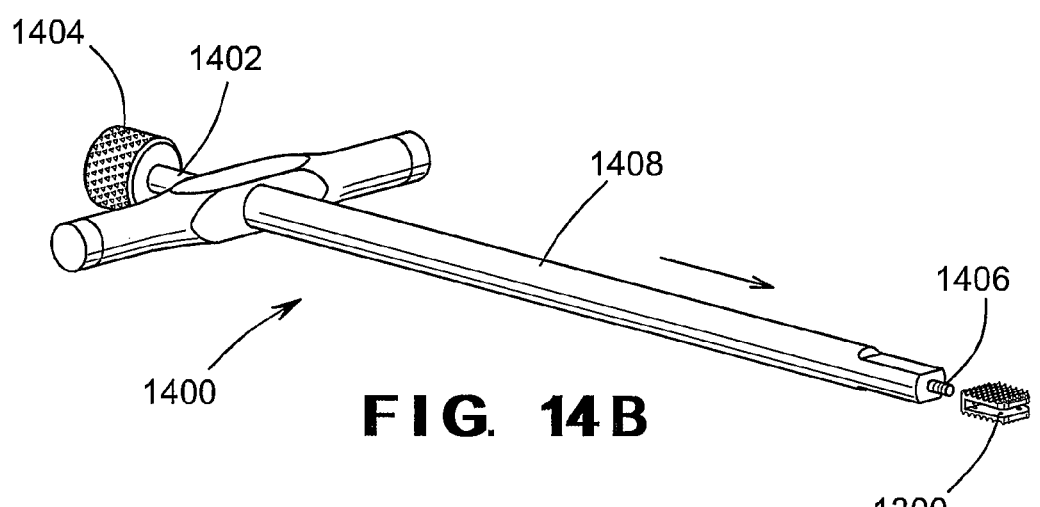
Figure 14C:
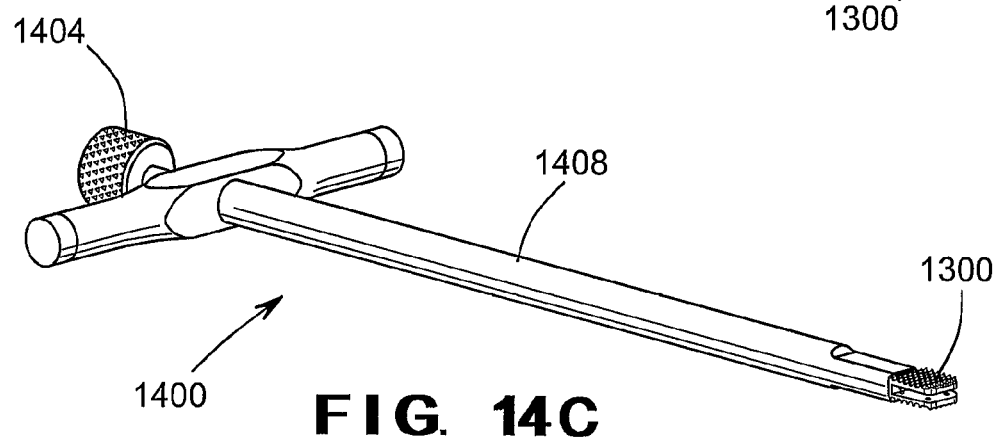

FIGS. 14A to 14C show a holder or impactor for deploying an embodiment of the distractor.

Figure 15A:
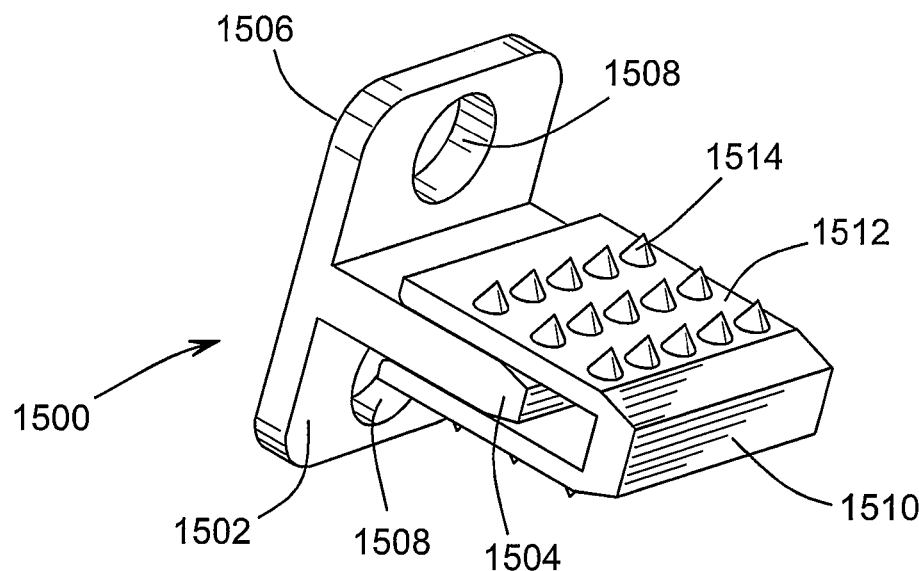
Figure 15B:
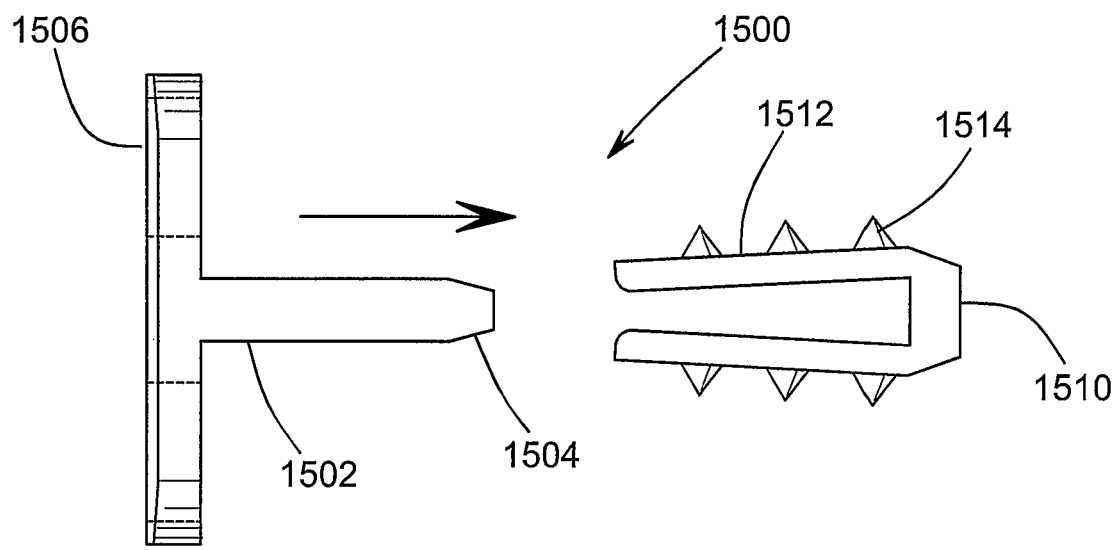

FIGS. 15A and 15B illustrate another embodiment of the distractor.

Figure 16A:
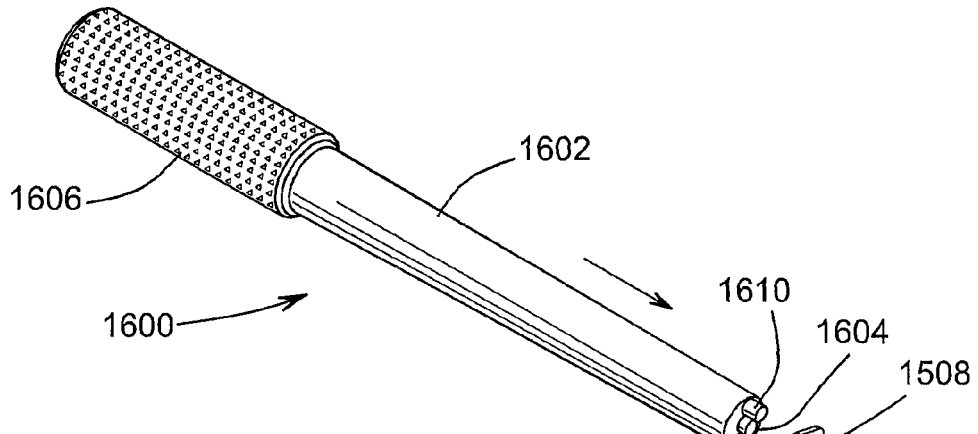
Figure 16B:
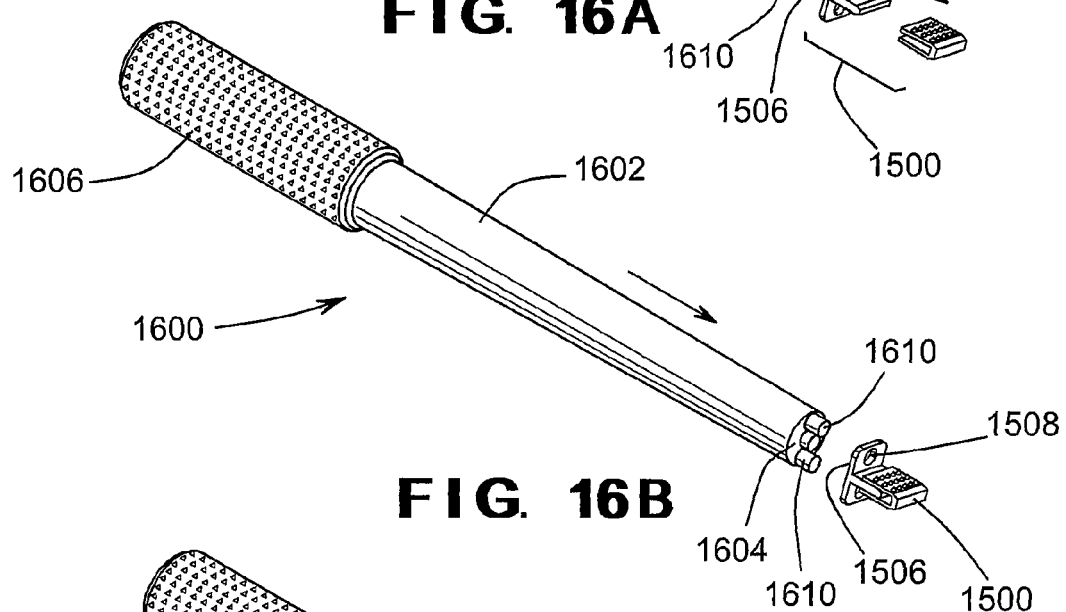
Figure 16C:
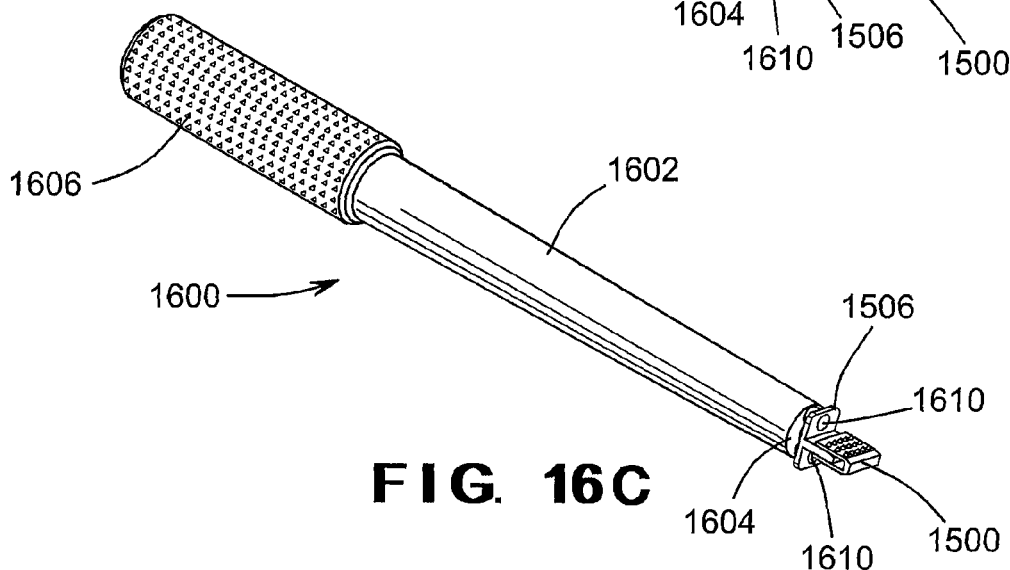

FIGS. 16A to 16C illustrate a holder for deploying an embodiment of the distractor.

Figure 17A:
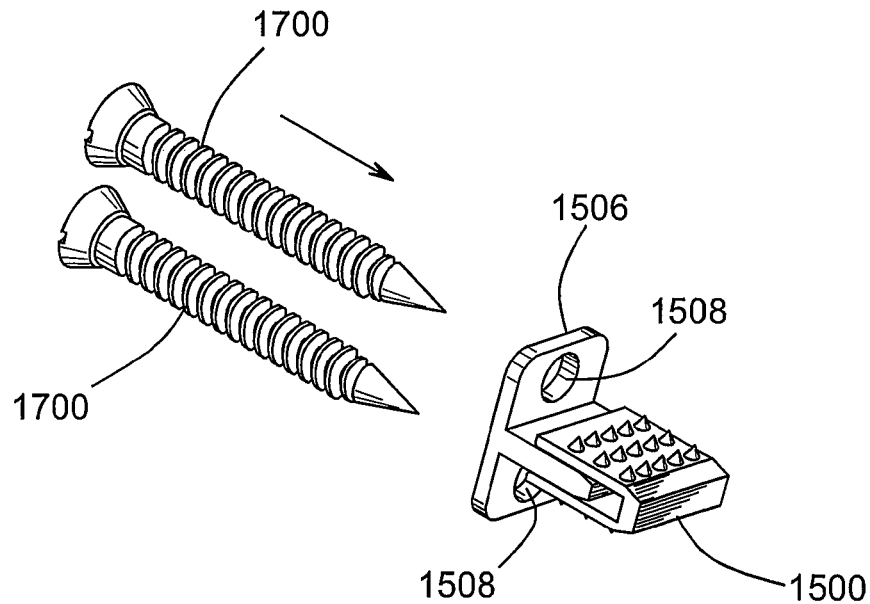
Figure 17B:
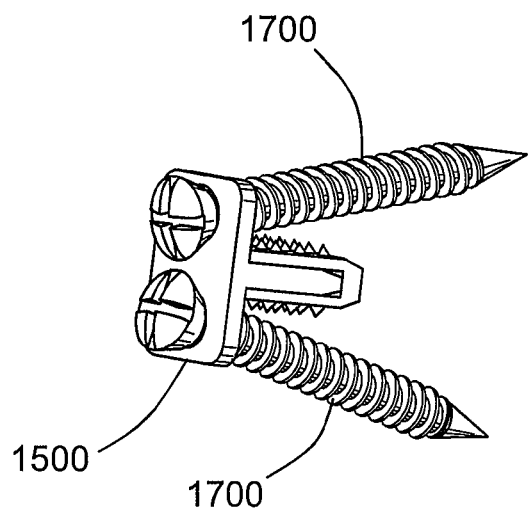
Figure 17C:
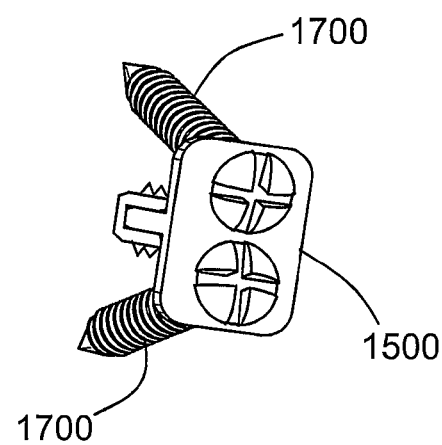

FIGS. 17A to 17C depict an embodiment of the distractor having means for affixing.

FIGS. 18A to 18D show a further embodiment of the distractor.

Figure 19A:
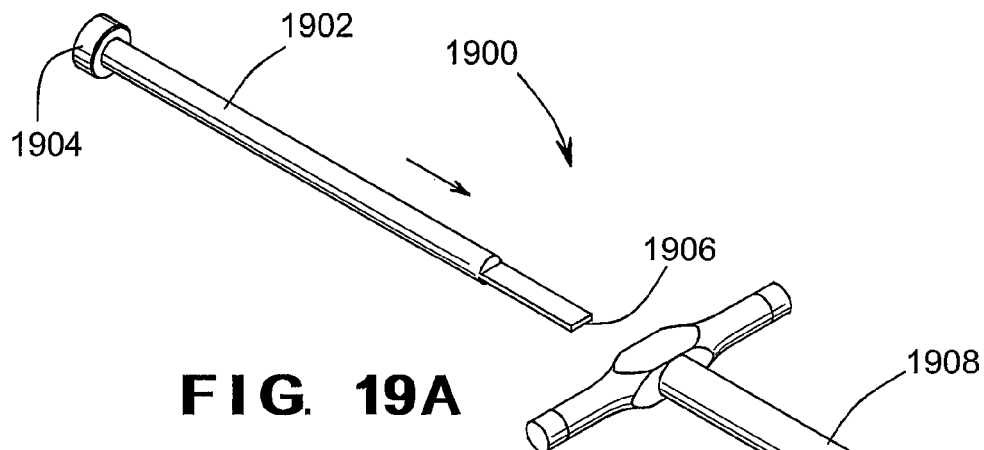
Figure 19B:
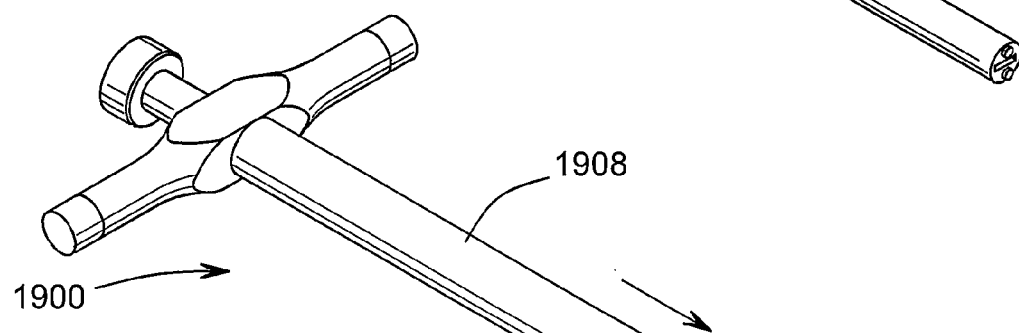
Figure 19C:
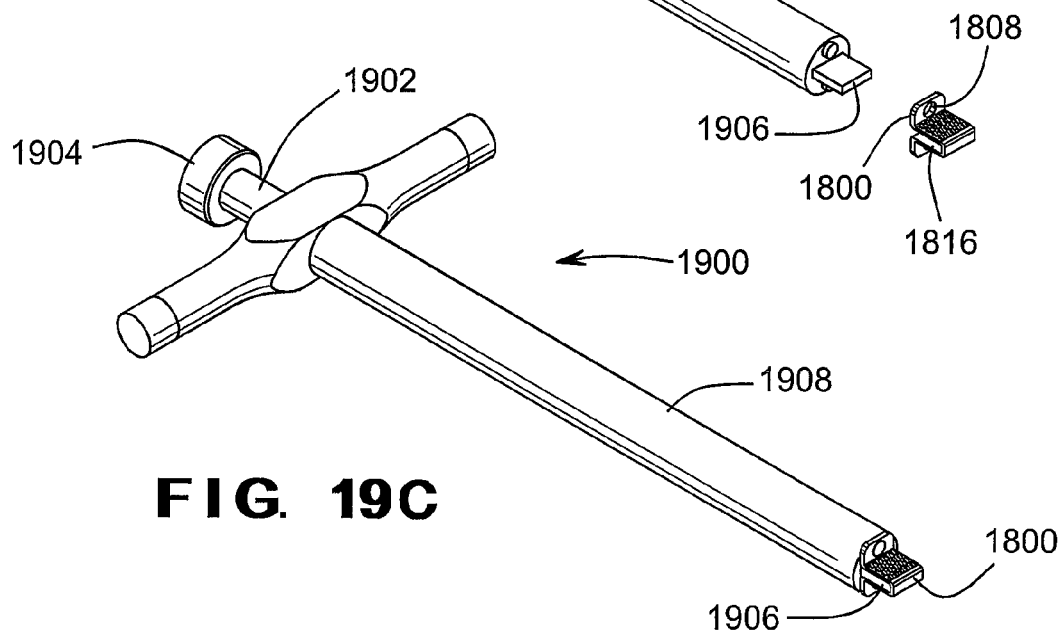

FIGS. 19A to 19C illustrate a holder for deploying an embodiment of the distractor.

Figure 20A:
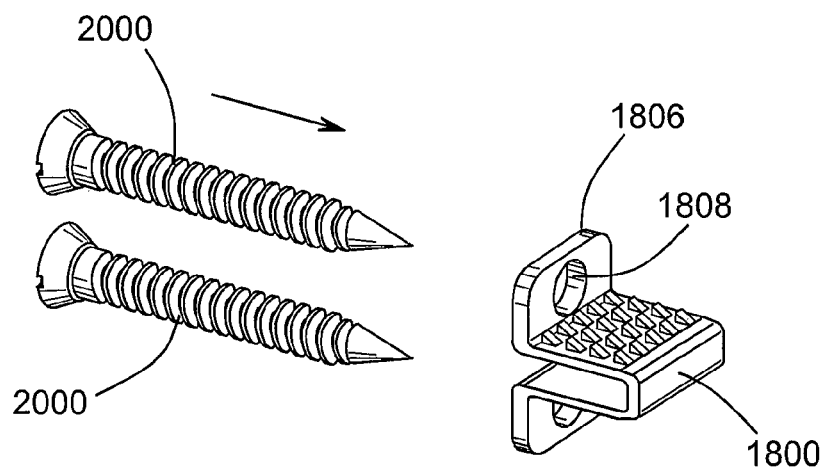
Figures 20B, 20C:
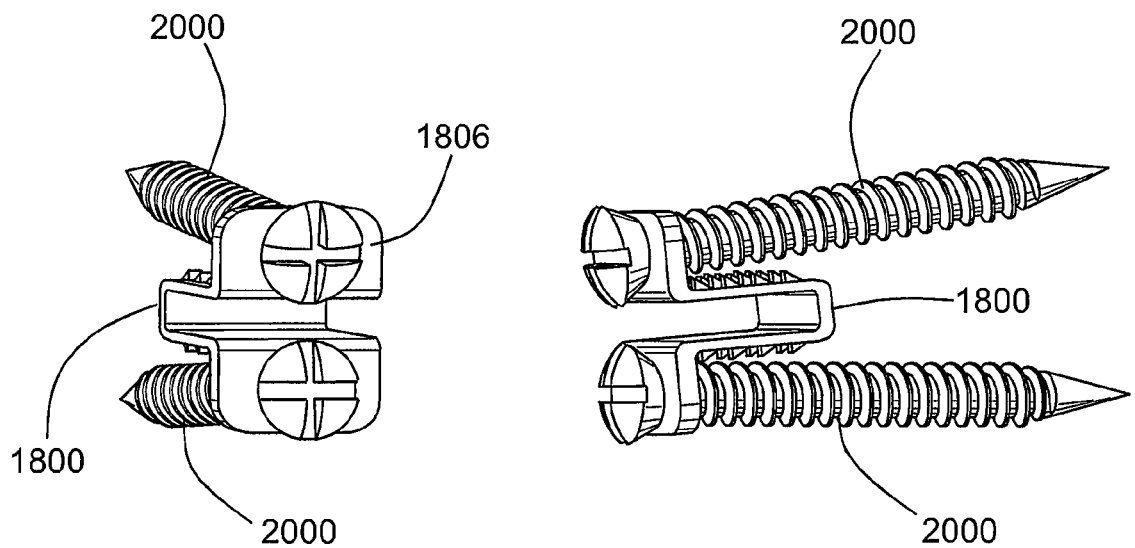

FIGS. 20A to 20C depict another embodiment of the distractor having means for affixing.

FIGS. 21A to 21D show a further embodiment of the distractor.

FIGS. 22A to 22J show other embodiments of the distractor.

Figure 23A:
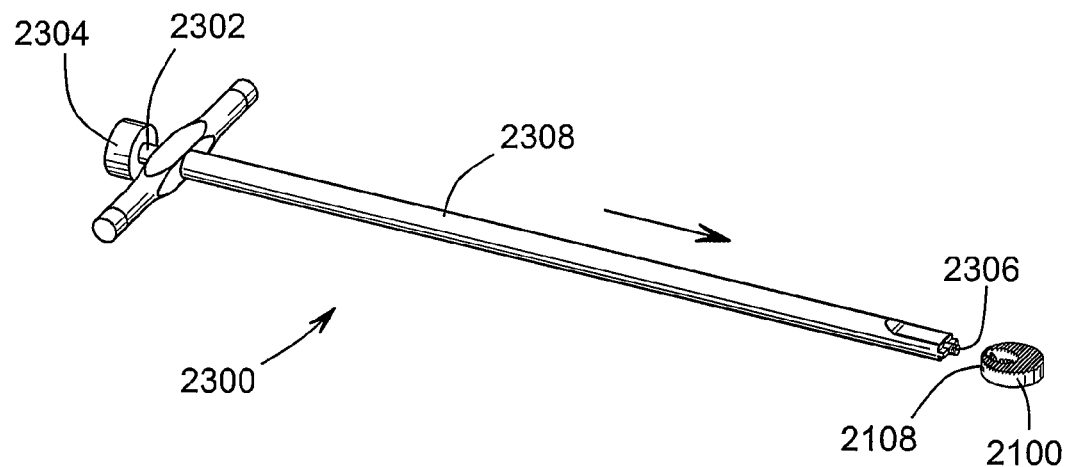
Figure 23B:
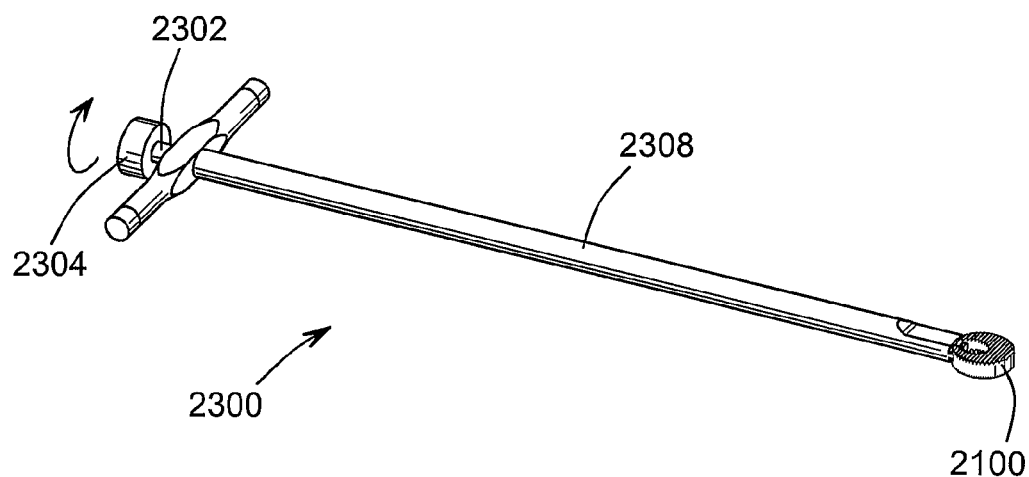

FIGS. 23A and 23B show a holder for deploying the distractor.

FIGS. 24A to 24E show a holder for deploying a particular embodiment of the distractor.

DETAILED DESCRIPTION OF THE INVENTION

The detailed description of the invention may be read with reference to the accompanying drawings. The drawings, which are not necessarily to scale, depict certain embodiments and are not intended to limit scope of the invention. The detailed description illustrates the invention by example, and not by limitation. The written description and drawings would enable the skilled person to make and use the invention.

Figure 1:
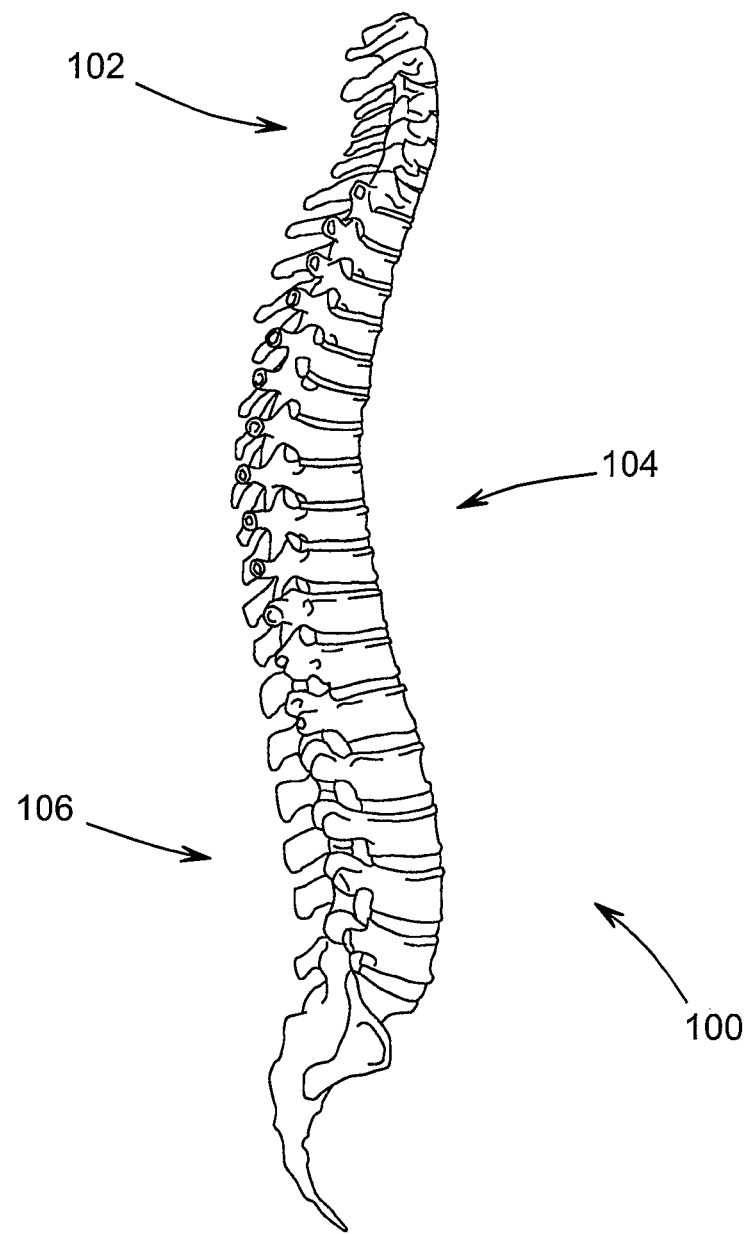
FIG. 1 illustrates the spine and spinal regions.

FIG. 1 is a representation of the spine 100, depicting the cervical region 102, thoracic region 104 and lumbar region 106. Depending on the region within which vertebral segments degenerate, spondylosis may be categorized as cervical, thoracic or lumbar.

The present invention is directed towards a device and method for treatment of spondylotic disease, including single-level and multi-level cervical and lumbar spondylotic disease.

It has been discovered that distraction (forced separation) of adjacent facets of the vertebra can lead to stabilization and fixation of the spinal segments and increase in space available for the spinal cord and spinal roots. The novel procedure has been found to result in reversal of all pathological events related to spondylotic disease. The invention provides a method and device for achieving distraction of vertebral facets located adjacent each other and consequent stabilization and fixation of spinal segments.

A joint in the anatomy is where two or more bones are joined. Joints facilitate motion (articulation) between bones. Joints in the spine are referred to as facet joints. Each vertebra has two sets of facet joints. One pair faces upward (superior articular facets), and the other pair faces downward (inferior articular facets). Each vertebra has two superior and inferior articular facets, one on each side. The junction of an inferior articular facet and the superior articular facet of the vertebra is referred to as an articular facet joint. Facet joints serve to link vertebrae together and permit relative movement therebetween.

Figure 2:
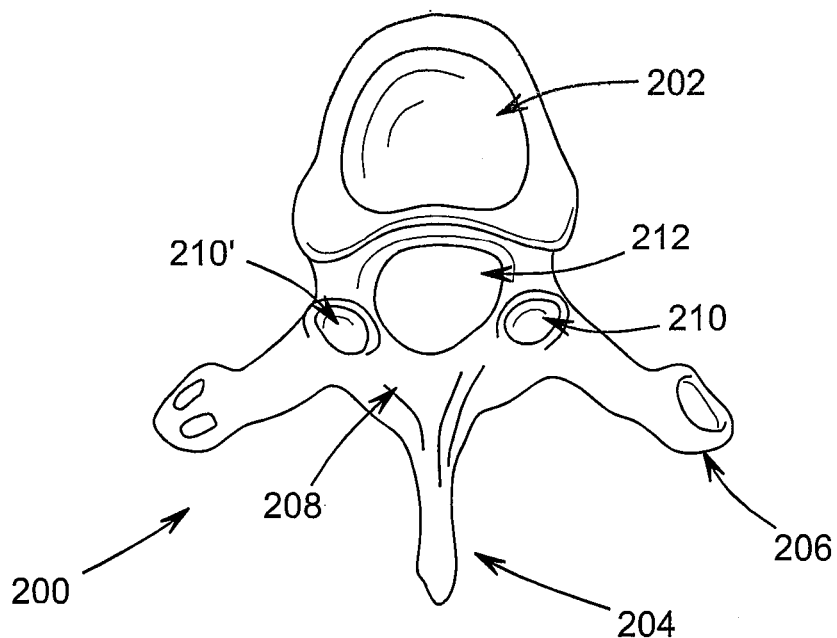
FIG. 2 illustrates a transverse section of a vertebra.

FIG. 2 illustrates a transverse section of a vertebra 200, having body 202, spinous process 204, transverse process 206, lamina 208 and spinal canal 212. Superior articular facets 210 and 210' are located on the upper surface of the vertebra. Though not visible in FIG. 2, a corresponding set of inferior articular facets are located on the lower surface of the vertebra. The inferior articular facets of a vertebra interface with the corresponding superior articular facets of the vertebra immediately below.

Figure 3:
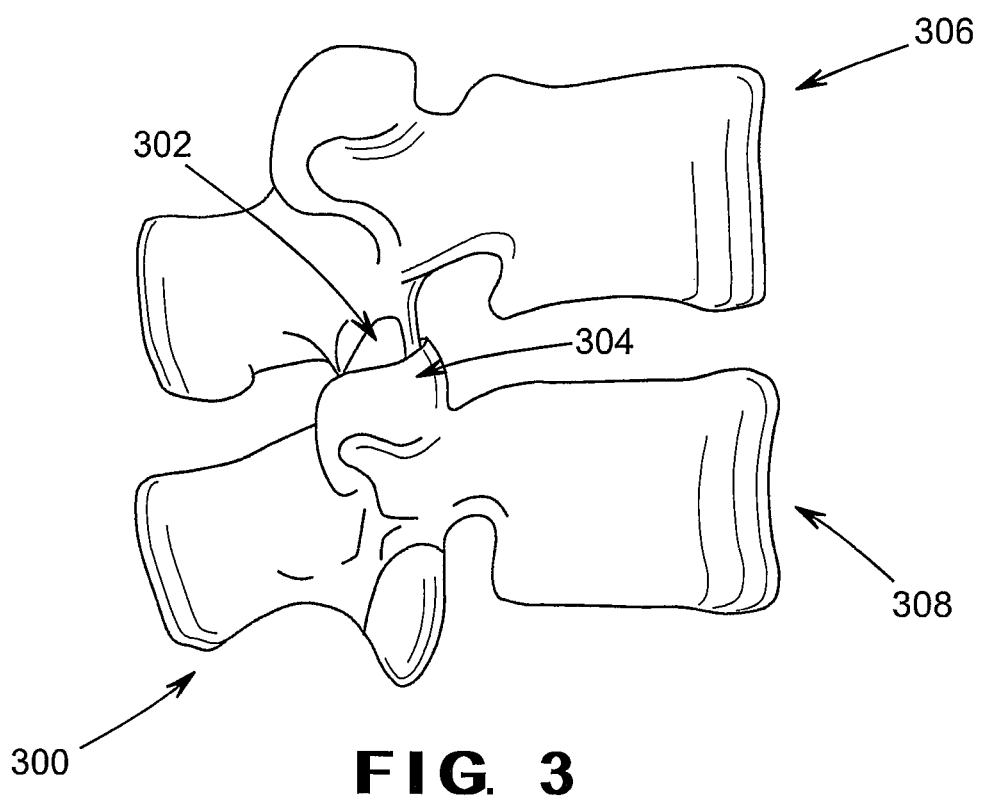
FIG. 3 shows the articular facets between adjoining lumbar vertebrae.

FIG. 3 illustrates a pair of adjoining lumbar vertebrae 300 wherein an inferior articular facet 302 of the upper vertebra 306 interfaces with a superior articular facet 304 of the lower vertebra.

Figure 4:
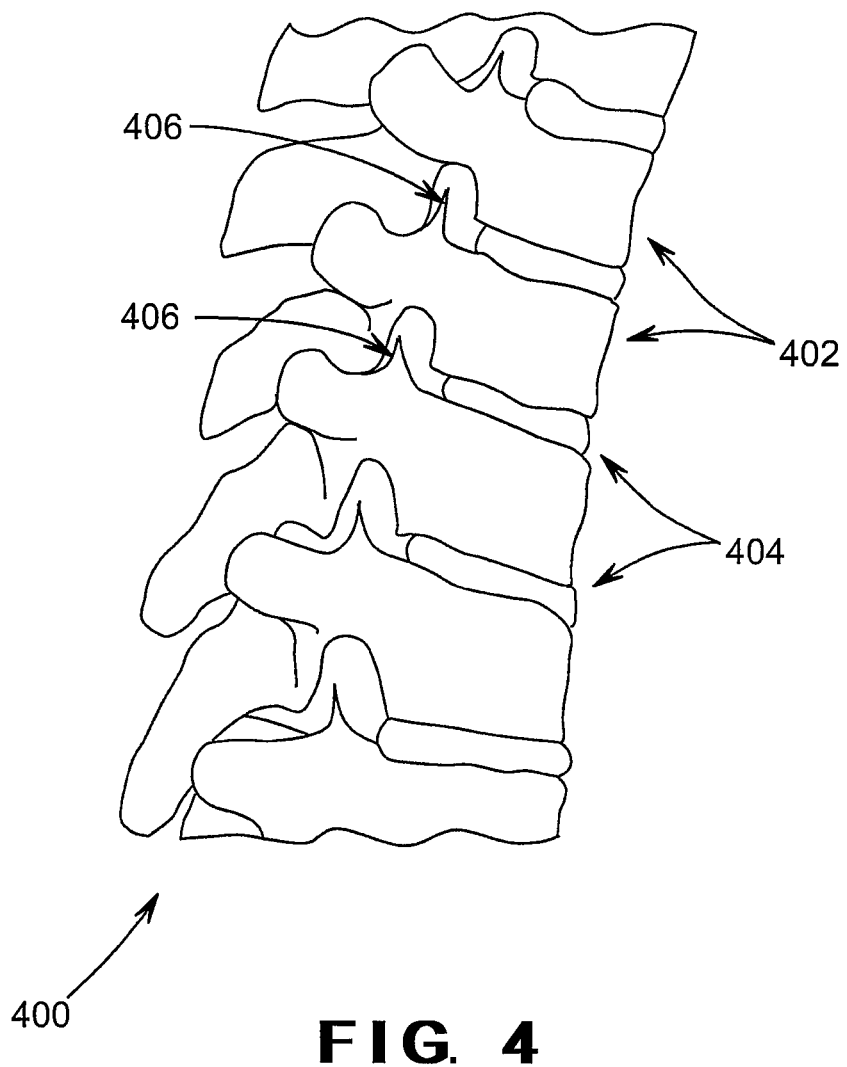
FIG. 4 depicts the anatomy of the spine and articular facets.

FIG. 4 illustrates the anatomy of the spine 400 comprising a plurality of vertebrae 402 with intervertebral discs 404 interspersed therebetween. Articular facet joints 406 are located at the junction of each vertebra with the vertebra immediately below.

Figure 5A:
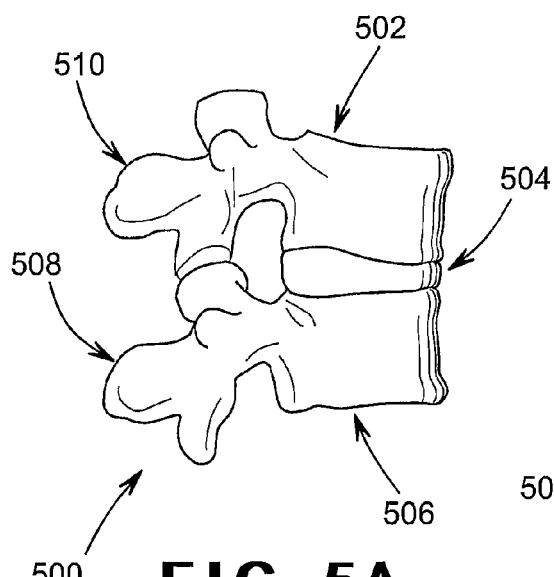
FIGS. 5A and 5B illustrate facet joints in motion during flexion and extension respectively.
Figure 5B:
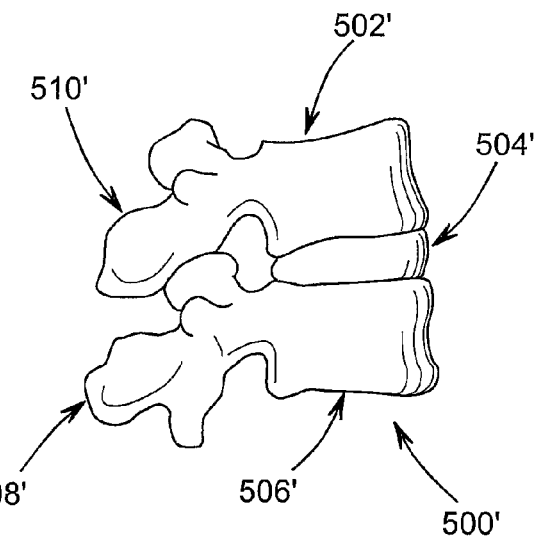

FIGS. 5A and 5B illustrate spinal segments 500 and 500', wherein facet joints of said spinal segments are in motion caused by movement of the spine. In FIG. 5A, the spine undergoes flexion (bending forward) wherein the spinous process 510 of upper vertebra 502 moves away from spinous process 508 of lower vertebra 506, causing the articular facets at the facet joint to move apart. In FIG. 5B, the spine undergoes extension (bending backward) wherein the spinous process 510' of upper vertebra 502' moves towards the spinous process 508' of lower vertebra 506', causing the articular facets at the facet joint to move closer together.

Figure 6:
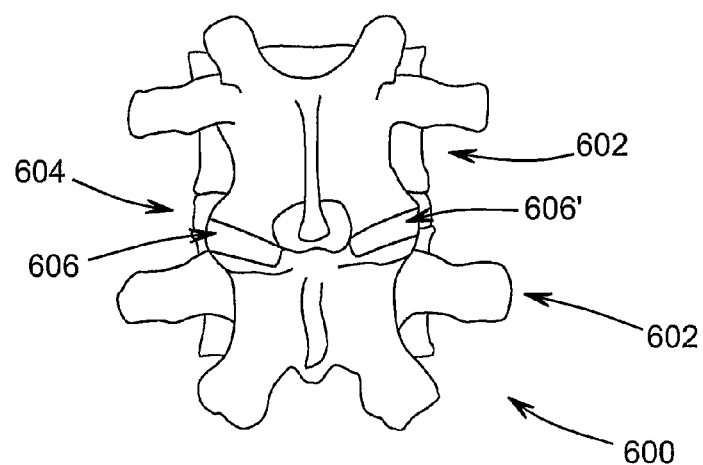
FIG. 6 illustrates adjoining vertebrae in the posterior spinal segment.

FIG. 6 illustrates a posterior view of the spinal segment 600, comprising a pair of adjoining vertebrae 602, having intervertebral disc 604 located therebetween, and facet joints 606 and 606' on the left and right side respectively at the junction between the upper and lower vertebrae.

It has been observed in cases of spondylotic disease that reduction in the disc space height, buckling of the posterior longitudinal ligament, buckling of the ligamentum flavum, reduction of diameter of spinal and root canal and retrolisthesis of the facets occur simultaneously. Notwithstanding the plurality of observable effects, the present invention relies on the unexpected finding that instability of the spinal segment may be paramount in pathogenesis of the entire structural deformation, and that reduction of inter-facet space height may present an important factor affecting stability. While prior art focuses on the theory that degenerative process initiated in the intervertebral discs results in osteophyte formation and retrolisthesis of facets, the present invention is based on the surprising discovery that spondylotic disease process begins with facetal instability, which thereafter involves degeneration of intervertebral discs.

The invention relies on stabilization of the spine to treat spondylotic disease, and more particularly upon distraction of the articular facets of adjacent vertebrae by implanting spacers within the articular cavities. It has been observed that implanting spacers within an articular cavity unexpectedly results in sustained traction and fixation of the spinal segment, while promoting local arthrodesis in the distracted position. Additionally, in comparison with previously known methods involving distraction of the vertebral bodies and spinous processes, or of placement of artificial discs in the vertebrae, the device and method of the present invention provide for a critical increase in space for the spinal cord and spinal roots, while achieving firm stabilization of the spine.

The method and device of the present invention simultaneously achieve distraction of the spinous processes and distraction of vertebral bodies. Additionally, implanting intra-facet articular distractors has been found to be significantly easier to perform than implants previously known in the art.

It has also been discovered that due to the direction of the bone profile, inter-spinous distraction results in a further decrease in the intervertebral height, as opposed to the articular joint distractors of the present invention (which result in an increase in the disc space height). Since reduction of intervertebral height has been found to have a significant impact on stability of the spine, increasing such height clearly provides a better solution over methods previously known in the art. Similarly, intervertebral body distractors (such as artificial discs) have been known to lead to foraminal narrowing, which may eventually lead to radiculopathy and myelopathy. In contrast, the method and device of the claimed invention has been found to reverse foraminal narrowing.

The present invention involves fusion of the spinal segments by promoting arthrodesis between the joints.

The device of the present invention comprises a distractor for distracting vertebral facets of first and second vertebrae located adjacent each other, at the articular joint. The distractor comprises a first abutment surface for interfacing with an inferior articular facet of the first vertebra and a second abutment surface for interfacing with the superior articular facet of the second vertebra, wherein the first and second abutments surfaces are, interconnected and separated by a predetermined distance. In an embodiment, the predetermined distance corresponds to the distraction intended for the articular facets.

The distractor may be constructed from a single unitary blank or molded structure or alternatively may comprise two abutment surfaces connected by at least one rigid connector, semi-rigid connector, sidewall or connecting medium. In an embodiment, the distractor is a spacer.

The distractor may have any one of a plurality of shapes and sizes based on the distraction sought to be achieved, and minimization of trauma to surrounding bone, tissue cartilage and the spinal cord and roots. The shape of the distractor may additionally be selected with a view to promote arthrodesis. The distractor may be provided with one or more of bores, holes, depressions and surface texturing with a view to assist in implanting and to improve arthrodesis. In an embodiment, the edges of the distractor may be rounded to reduce trauma to surrounding regions of bone, tissue and nerves.

FIGS. 7A to 7D illustrate top, perspective and side views of an embodiment of the distractor 700, wherein said distractor has a cylindrical contour having opposed top and bottom surfaces 702 and 704, outer sidewall 706, inner sidewall 714, and a central lumen 712. Outer sidewall 706 and inner sidewall 714 are connected by a bore having opening 708 on outer sidewall 706 and opening 710 on inner sidewall 714.

Opposed top and bottom surfaces 702 and 704 of distractor 700 serve to interface with the superior and inferior articular facets of the articular joint sought to be distracted. Central lumen 712 connects top and bottom surfaces 702 and 704 and promotes arthrodesis by allowing bone formation through the distractor. The bore having openings 708 and 710 allows for a holder to be affixed to the distractor for insertion into the articular joint. It would however be understood that the bore need not connect the inner and outer sidewalls of the distractor, and may instead comprise a recess only extending partly thereinto, to allow a holder to be affixed. In a preferred embodiment the bore is provided with screw threads, grooves or other connectors that engage with corresponding screw threads, grooves or connectors on the holder to facilitate engagement between the holder and distractor.

FIGS. 8A to 8C illustrate a holder 800 for inserting the distractor 700 into an articular joint. The holder comprises an elongated cylindrical body 802 for gripping, and a tip 804 for engaging with the bore in distractor 700 through opening 708. In an embodiment, tip 804 may be provided with screw threads or other means for engaging with distractor 700.

Figure 9A:
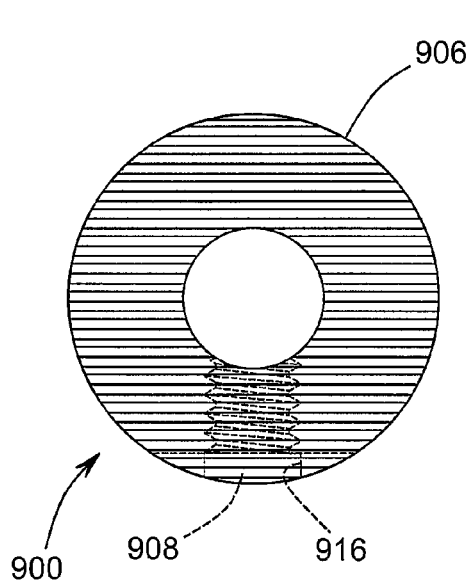
Figure 9B:
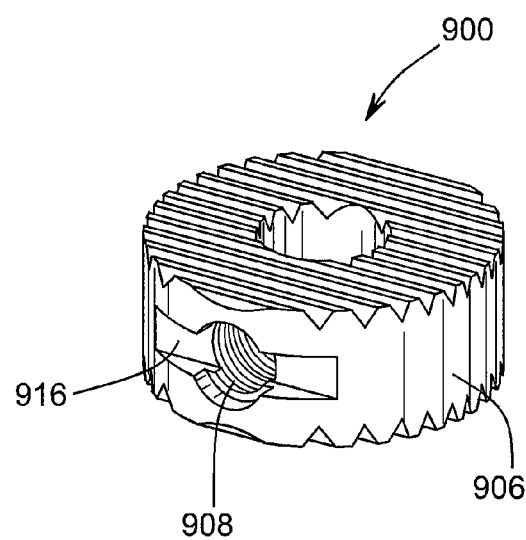
Figure 9C:
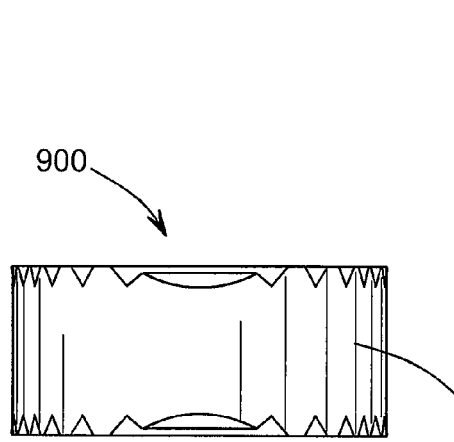
Figure 9D:
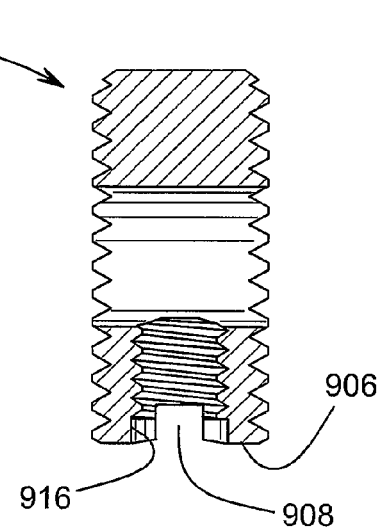

FIGS. 9A to 9D illustrate a preferred embodiment of the distractor 900 previously illustrated in FIGS. 7A to 7D, with the additional feature that the outer sidewall 906 is provided with at least one notch 916 thereon. In the embodiments of FIGS. 9A, 9B and 9D, the notch is provided in the vicinity of (and surrounding) the opening 908 on outer sidewall 906. Notch 916 assists in stabilizing engagement between distractor 900 and a holder during the implant procedure.

FIGS. 10A to 10D illustrate another embodiment of a holder 1000 for inserting distractor 900 in the facet joint between vertebrae.

The illustrated holder comprises an elongated inner cylindrical body 1002 having head portion 1004 and tip 1006 for engaging with the bore in distractor 900 through opening 908. In an embodiment, tip 1006 may be provided with a chisel tip or other flat edge so as to engage with notch 916 on distractor 900.

The holder additionally comprises an outer T-shaped sleeve 1008, capable of allowing cylindrical body 1002 or a substantial part thereof to reside therewithin, such that tip 1006 protrudes from one end of the outer sleeve 1008 to engage with distractor 900.

FIGS. 11A to 11C illustrate an embodiment of the distractor 1100, having an elongated cylindrical contour having opposed top and bottom surfaces 1102 and 1104, outer sidewall 1106, inner sidewall 1114, and a central lumen 1112 having opening 1114 in bottom surface 1104. Outer sidewall 1106 may be provided with screw threads 1108 or other surface irregularities to promote bone fusion.

FIGS. 12A and 12B illustrate a holder 1200 for inserting distractor 1100 between vertebrae. The holder comprises an elongated cylindrical body 1202 for gripping, and a tip 1204 for engaging with opening 1114 in distractor 1100. In an embodiment, tip 1204 may be provided with screw threads or other means for engaging with distractor 1100. In another embodiment, tip 1204 may rely on an interference fit with opening 1114 for engaging with distractor 1100.

FIGS. 13A to 13D illustrate an embodiment of distractor 1300, comprising upper plate 1302 and lower plate 1304, interconnected by connecting member 1306. Seen from the side in FIG. 13C, distractor 1300 has a first end 1310 and a second end 1312, wherein distance d1 between upper plate 1302 and lower plate 1304 at first end 1310 is greater than distance d2 between upper plate 1302 and lower plate 1304 at second end 1312. The tapering configuration provided by this arrangement assists in affixing distractor 1300 between adjoining articular facets and also in altering the spinal curvature when necessary. The upper plate 1302 and, lower plate 1304 of distractor 1300 may be provided with surface irregularities 1314 for promoting bone fusion.

In an embodiment, connecting member 1306 is provided with a bore having opening 1308 for accommodating a distractor holder.

FIGS. 14A to 14C illustrate another embodiment of holder 1400 for inserting distractor 1300 between vertebrae.

Holder 1400 comprises an elongated inner cylindrical body 1402 having head portion 1404 and tip 1406 for engaging with the bore in distractor 1300 through opening 1308. In an embodiment, tip 1406 may be provided with screw threads or other means for engaging with distractor 1300.

The holder additionally comprises an outer T-shaped sleeve 1408, capable of allowing cylindrical body 1402 or a substantial part thereof to reside therewithin, such that tip 1406 protrudes from one end of the outer sleeve 1408 to engage with distractor 1300.

FIGS. 15A and 15B illustrate another embodiment of the distractor. Distractor 1500 comprises t-shaped member 1502 having anterior end 1504 and posterior end 1506. Anterior end 1504 is intended for being positioned in the facet joint between the articular facets. In an embodiment posterior end 1506 is provided with one or more holes 1508 capable of engaging with a holder, or for accommodating screws for affixing the distractor to the vertebrae.

In a particular embodiment, distractor 1500 further comprises u-shaped member 1510, capable of being fitted onto anterior end 1504 of t-shaped member 1502. When u-shaped member 1510 is fitted onto t-shaped member 1502, the increased overall dimensions of distractor 1500 serves to increase the distraction of the articular facets.

In an embodiment, the outer surface 1512 of u-shaped member 1510 is provided with surface irregularities 1514 for promoting bone fusion.

FIGS. 16A to 16C illustrate a holder 1600 for inserting distractor 1500 between vertebrae. The holder comprises an elongated cylindrical body 1602 with a first end 1606 textured for gripping, and a tip 1604 for engaging with holes 1508 provided in posterior end 1506 of distractor 1500. In an embodiment, tip 1604 may be provided with multiple prongs 1610 for engaging with distractor 1500. In another embodiment, tip 1604 may rely on screw threads or an interference fit for engaging with distractor 1500.

FIGS. 17A to 17C illustrate using screws for fastening distractor 1500 to the vertebrae. One or more screws 1700 are inserted into corresponding one or more holes 1508 provided in posterior end 1506 of distractor 1500. The screws 1700 may thereafter be angled appropriately depending on the location of the vertebrae to which they are intended to be affixed.

FIGS. 18A to 18D illustrate another embodiment of the distractor. Distractor 1800 comprises a u-shaped member having anterior end 1804 and posterior end 1806. Anterior end 1804 is intended for being positioned in the articular facet joint between the articular facets. In an embodiment posterior end 1806 is provided with one or more flanges 1810. Flanges 1810 may optionally be provided with one or more holes 1808 capable of engaging with a holder, or for accommodating screws for affixing the distractor to the vertebrae.

In an embodiment, the outer surface 1812 of distractor 1800 is provided with surface irregularities 1814 for promoting bone fusion.

FIGS. 19A to 19C illustrate another embodiment of a holder 1900 for inserting distractor 1800 between vertebrae.

Holder 1900 comprises an elongated inner cylindrical body 1902 having head portion 1904 and tip 1906 for engaging with distractor 1800 through holes 1808. In an embodiment, tip 1906 may comprise a chisel head for engaging with the u-shaped recess 1816 in distractor 1800.

Holder 1900 additionally comprises an outer T-shaped sleeve 1908, capable of allowing cylindrical body 1902 or a substantial part thereof to reside therewithin, such that tip 1906 protrudes from one end of the outer sleeve 1908 to engage with distractor 1800.

FIGS. 20A to 20C illustrate using screws for fastening distractor 1800 to the vertebrae. One or more screws 2000 are inserted into corresponding one or more holes 1808 provided in posterior end 1806 of distractor 1800. The screws 2000 may thereafter be angled appropriately depending on the location of the vertebrae to which they are intended to be affixed.

FIGS. 21A to 21D illustrate an embodiment of the distractor 2100, wherein said distractor has a cylindrical contour having opposed top and bottom surfaces 2102 and 2104, the top surface 2102 defined by a flat first plane AA and the bottom surface 2104 defined by a flat second plane BB, outer sidewall 2106, inner sidewall 2114, bore having opening 2108 in outer sidewall 2106, and a central lumen 2112, wherein the axis of central lumen 2112 is angled with respect to the flat first and second planes AA and BB of the top and bottom surfaces 2102 and 2104 of distractor 2100. The angled central lumen 2112 permits for angling of a screw through the central lumen into an adjoining articular facet for securely affixing the distractor. In a preferred embodiment, angled central lumen 2112 permits for a screw to affix distractor 2100 in a "trans-articular" configuration i.e. wherein the screw passes through each of the adjoining superior and inferior articular facets and also through angled central lumen 2112 of distractor 2100. In a preferred embodiment, angled central lumen 2112 is at an angle of 45° with respect to the flat first and second flat planes AA and BB of the top and bottom surfaces 2102 and 2104 of distractor 2100. In an embodiment, the distractor 2100 may further be provided with notch 2116 on outer sidewall 2106 for promoting arthrodesis. It has been discovered that affixing distractor 2100 in the trans-articular configuration is particularly useful in stabilizing the distractor in the lumbar region.

The embodiments in FIGS. 21A to 21D, and throughout the invention may be varied by texturing at least one surface of the distractor with a view to assist fixation of the distractor. The textured may include one or both of the two abutment surfaces. In a more specific embodiment, texturing of the at least one surface is achieved by providing grooves, channels, spikes, knobs, bumps, protrusions, depressions or any other surface irregularity that would promote fixation.

FIGS. 22A to 22F illustrate an embodiment of distractor 2200, comprising upper plate 2202 and lower plate 2204. Upper plate 2202 has outer surface 2206 and inner surface 2208. Lower plate 2204 is provided with outer surface 2210 and inner surface 2212. Upper plate 2202 and lower plate 2204 are connected or engaged inter se in a manner so as to permit movement of one relative to the other. Depending on the manner of connection or engagement therebetween, upper plate 2202 and lower plate 2204 are permitted to move relative to each other along one or more o f the x, y and z axes.

In the embodiment shown in FIGS. 22C to 22F, inner surface 2212 of lower plate 2204 is provided with protrusion 2214. Inner surface 2208 of upper plate 2202 is provided with a corresponding recess 2216, capable of partially or fully housing protrusion 2214. When inner surface 2208 and inner surface 2212 are brought into contact, protrusion 2214 engages with corresponding recess 2216 in a ball and socket configuration that permits for relative movement of upper plate 2202 and lower plate 2204 with respect to each other. The protrusion 2214 and recess 2216 may be respectively sized to permit engagement with the desired amount of play therebetween.

FIGS. 22E to 22H illustrate the manner in which upper plate 2202 and lower plate 2204 are permitted to move relative to each other by virtue of the ball and socket engagement therebetween.

Figure 22G:
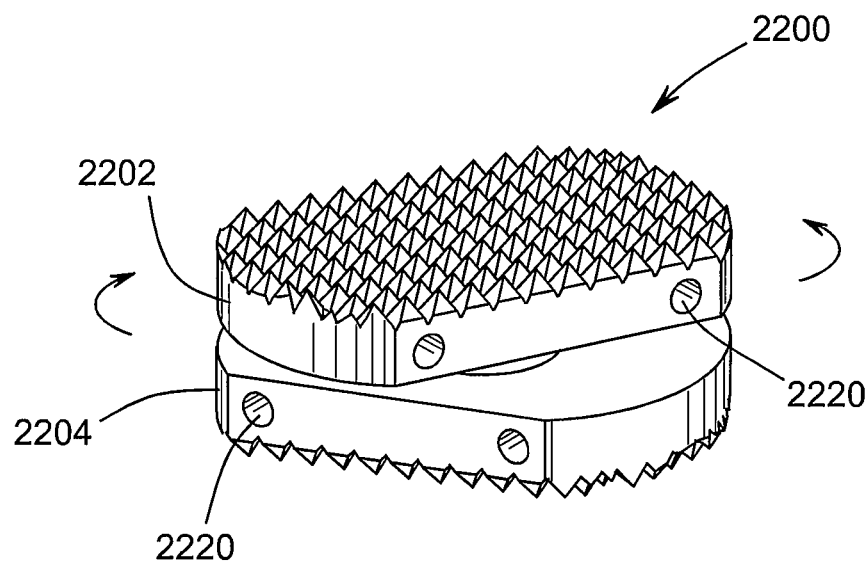
Figure 22H:
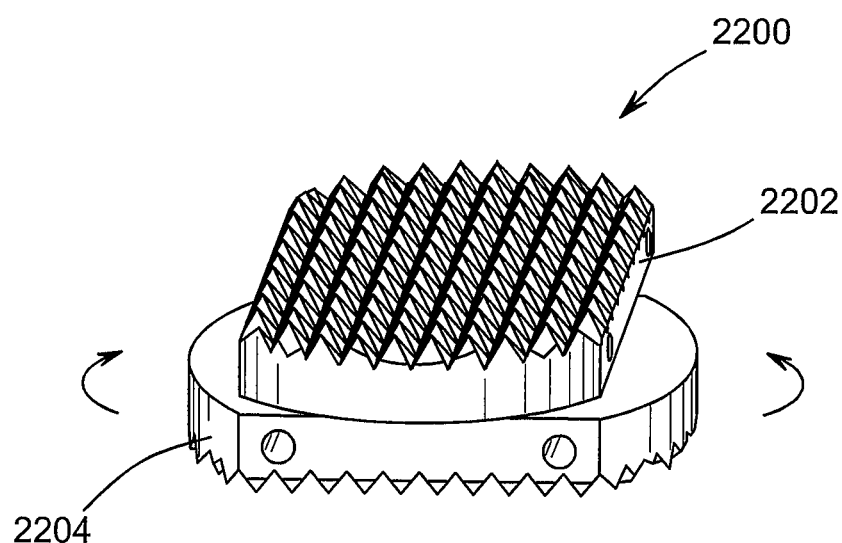
Figure 22I:
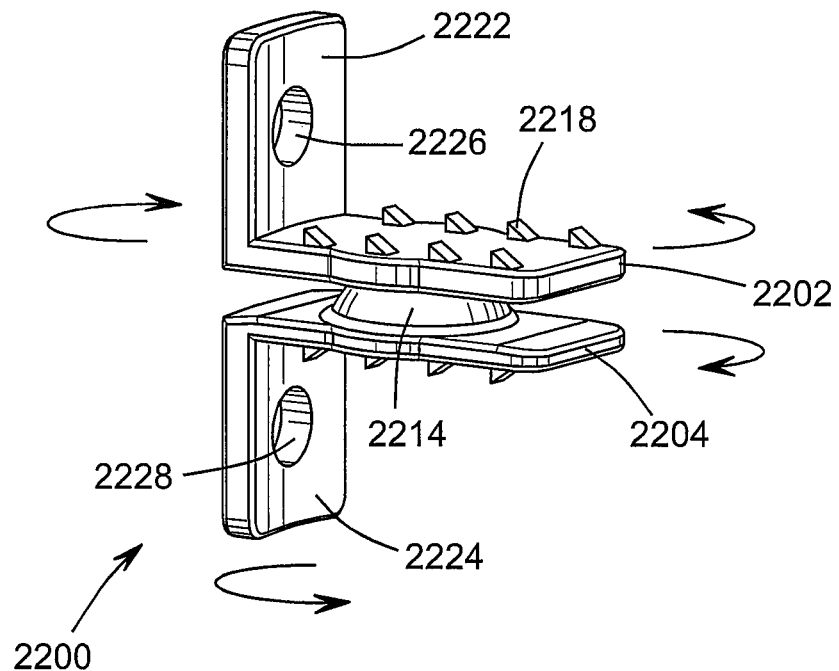
Figure 22J:
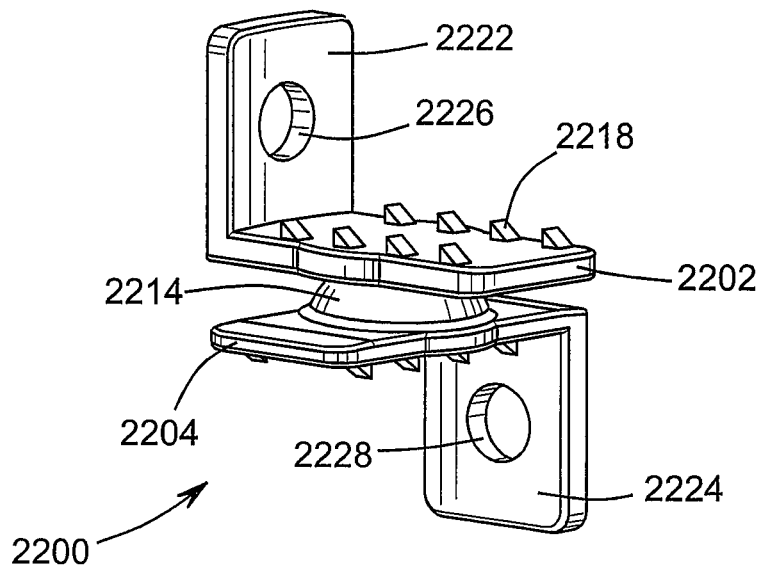

FIGS. 22I and 22J illustrate an embodiment of distractor 2200, whererein upper plate 2202 and lower plate 2204 are respectively provided with flanges 2222 and 2224. Flanges 2222 and 2224 are respectively provided with holes 2226 and 2228 that are capable of engaging with a holder, or for accommodating screws for affixing the distractor to the vertebrae. It has been discovered that the embodiment illustrated in FIGS. 22I and 22J is particularly effective for high cervical fixation (involving the C1 and C2 cervical vertebrae).

It would be immediately appreciated that the relative movement between the upper and lower abutment surfaces of distractor 2200 significantly improves performance of the distractor i n flexion and extension movements, and reduces the loss of flexibility that may arise in case of a unitary distractor.

Additionally, while distractor 2200 has been depicted with a ball and socket engagement between the upper and lower abutment surfaces, other engagement members, including one or more resilient connectors, elastic connectors, springs, pivoting joints and hinges would immediately suggest themselves to the skilled person seeking to engage an upper and lower plate so as to permit movement relative each other.

In the illustrated embodiments, upper plate 2202 and lower plate 2204 of distractor 2200 may be provided with surface irregularities 2218 for promoting bone fusion. The plates are additionally provided with one or more recesses 2220, for engaging with prongs or tips of holders to enable placement of the distractor between the articular facets.

FIGS. 23A and 23B illustrate an embodiment of a holder 2300 for inserting distractor 2100 between vertebrae.

Holder 2300 comprises an elongated inner cylindrical body 2302 having head portion 2304 and tip 2306 for engaging with distractor 2100 through hole 2108. Tip 2306 may be appropriately configured (e.g. screw tip, prongs, chisel head configuration etc.) to appropriately fit the shape of hole 2108 in distractor 2100.

Holder 2300 additionally comprises an outer T-shaped sleeve 2308, capable of allowing cylindrical body 2302 or a substantial part thereof to reside therewithin, such that tip 2306 protrudes from one end of the outer sleeve 2308 to engage with distractor 2100.

FIGS. 24A to 24E illustrate another embodiment of holder 2400 for inserting distractor 2100 in a trans-articular configuration between adjoining vertebrae, for affixing the distractor by means of a screw.

Holder 2400 comprises an elongated inner cylindrical body 2402 having head portion 2404 and tip 2406 for engaging with distractor 2100 through opening 2108. Tip 2406 may be appropriately configured (e.g. having any one of a screw tip, prongs, chisel head configuration etc.) to appropriately fit the shape of opening 2108 in distractor 2100.

Holder 2400 additionally comprises an outer cylindrical sleeve 2408, capable of allowing cylindrical body 2402 or a substantial part thereof to reside therewithin, such that tip 2406 protrudes from one end of outer sleeve 2408 to engage with distractor 2100.

Outer cylindrical sleeve 2408 has angled arm 2410 affixed thereto. Angled arm 2410 comprises a first arm section 2412 affixed to outer cylindrical sleeve 2408. First arm section 2412 has a first end 2416 and a second end 2418. First end 2416 is affixed to outer cylindrical sleeve 2408 perpendicular or substantially perpendicular thereto. Angled arm 2410 additionally comprises a second arm section 2414 having a first end 2420 and a second end 2422. First end 2420 of second arm section 2414 is affixed to second end 2418 of first arm section 2412, at an angle a to form an elbow. In an embodiment, angle a is capable of being adjusted. In a preferred embodiment angle a is the same as or substantially the same as the angle of central lumen 2112 of distractor 2100.

Second arm section 2414 comprises a cylindrical sleeve having first opening 2424 and second opening 2426. The configuration of second arm section 2414 enables drill bit 2428 and driver 2430 to be interchangeably housed within second arm section 2414. In the embodiment where angle a is the same as or substantially the same as the angle of central lumen 2112 of distractor 2100, the configuration of angled arm 2410 enables drill bit 2428 or driver 2430 to traverse a path coincident with the axis of angled central lumen 2112 when distractor 2100 has been affixed to holder 2400.

Figure 24A:
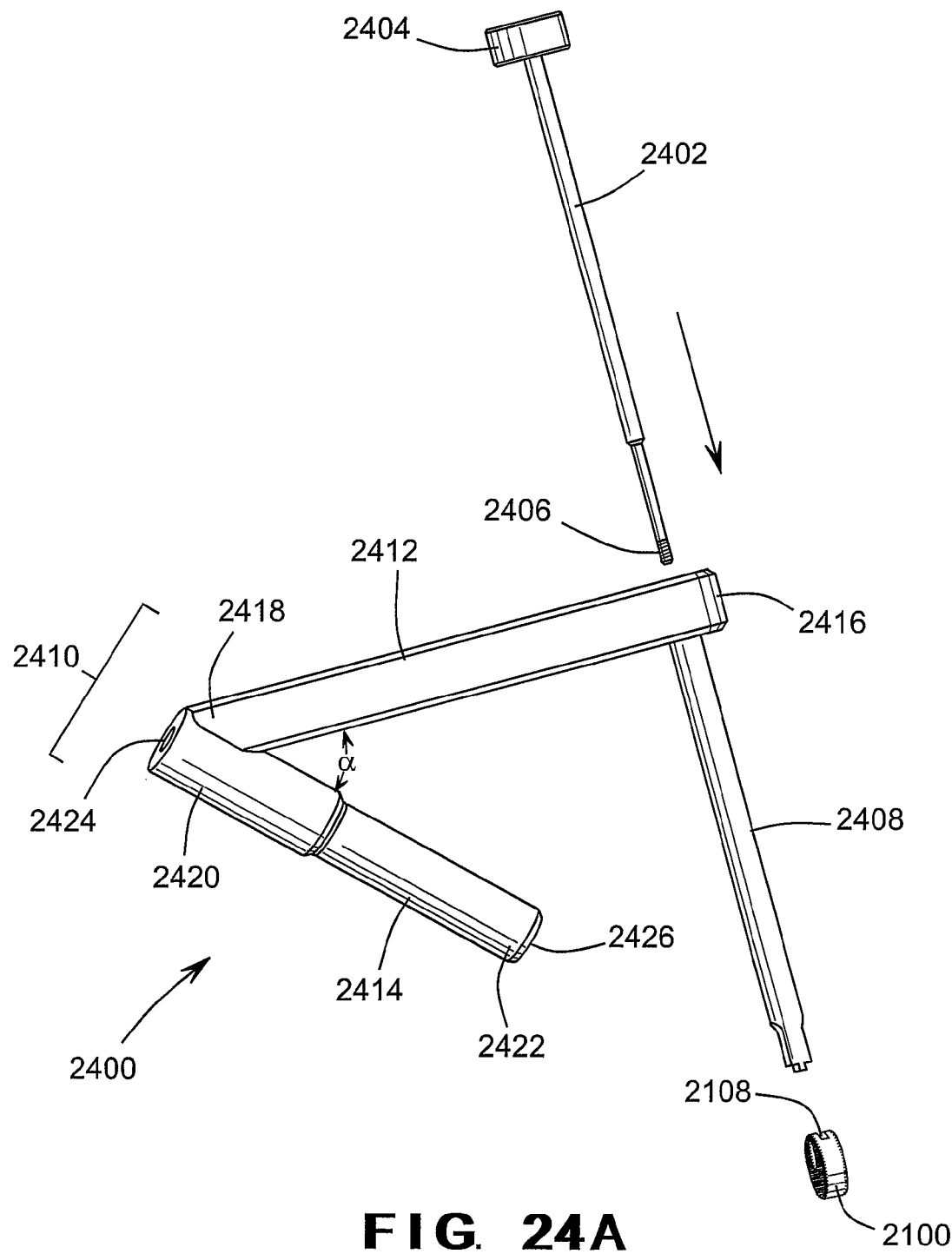
Figure 24B:
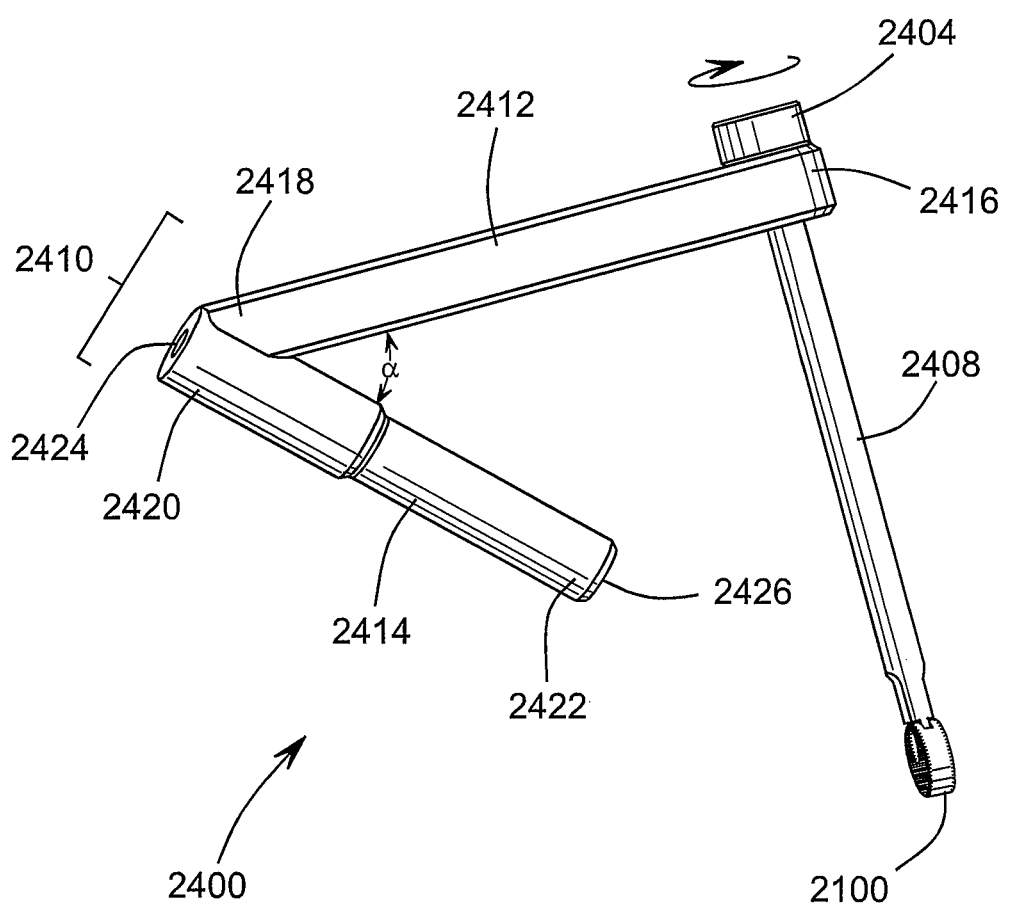
Figure 24C:
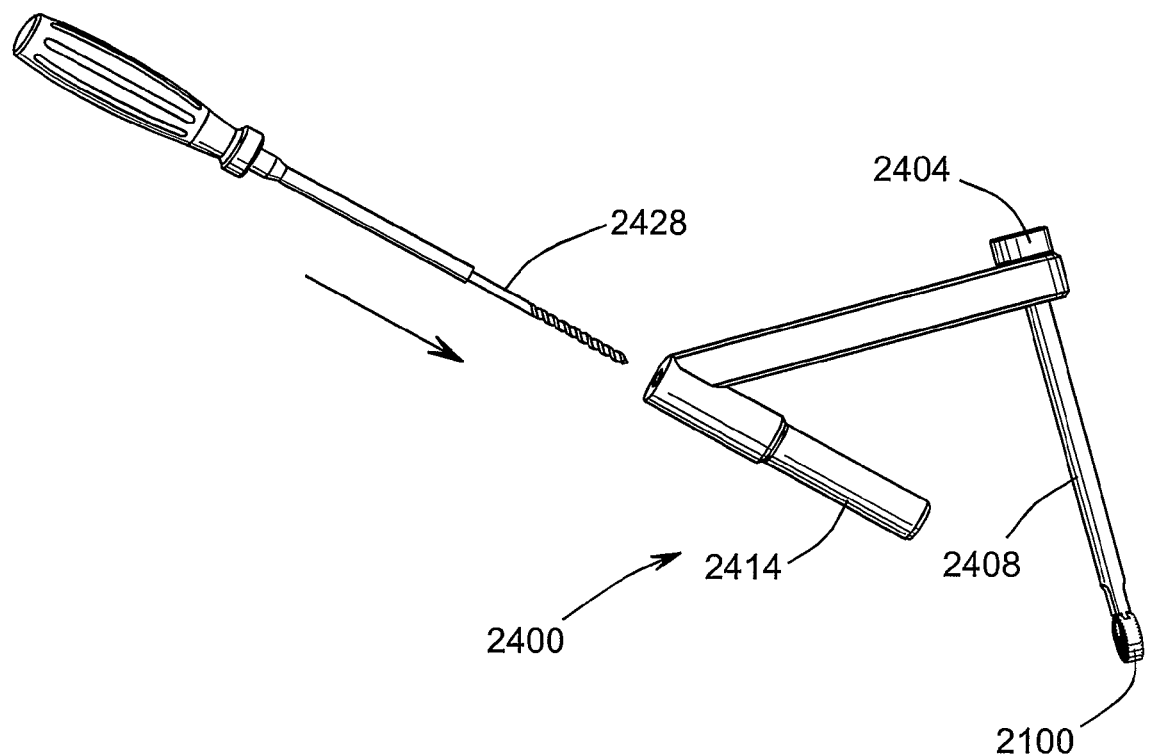
Figure 24D:
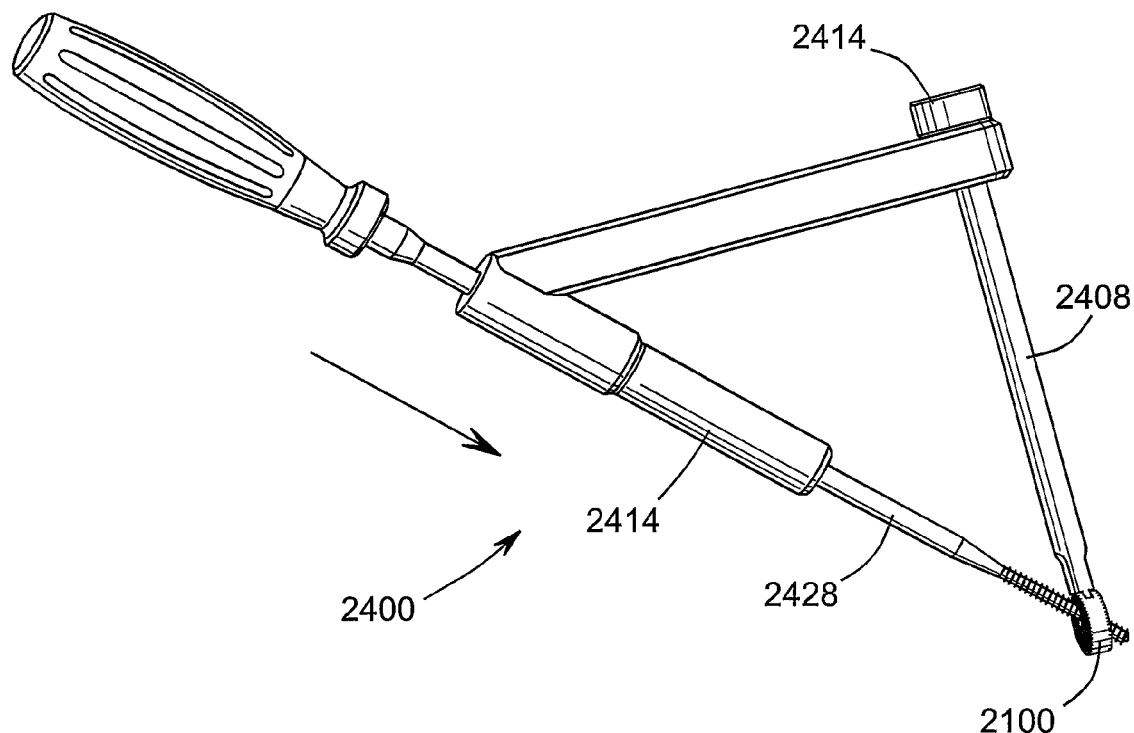

FIGS. 24C and 24D illustrate an embodiment of holder 2400, wherein second arm section 2414 houses drill bit 2428, such that drill bit 2428 traverses a path coincident with the axis of angled central lumen 2112 when distractor 2100 has been affixed to holder 2400. It would be immediately understood that this arrangement permits for the holder to implant distractor 2100 into an intra-articular facet joint, while drill bit 2428 is simultaneously used to drill through one of the two vertebral facets forming the intra-articular facet joint, pass through angled central lumen 2112 of distractor 2100, and finally drill through the other of the two vertebral facets corresponding to the intra-articular facet.

Figure 24E:
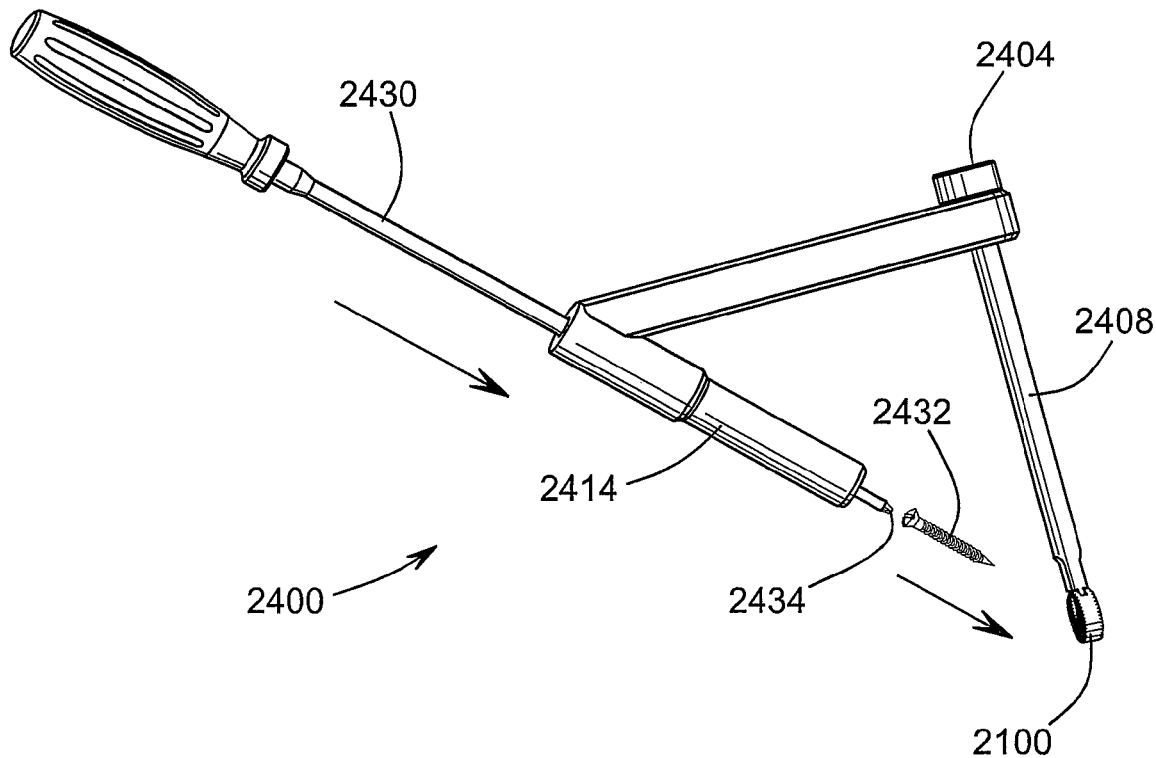

As illustrated in FIG. 24E, drill bit 2428 may thereafter be replaced by driver 2430 for driving a screw 2432 or other connector through the vertebral facets and the distractor. In the illustrated embodiment, second arm section 2414 of holder 2400 houses driver 2430, such that driver 2430 traverses a path coincident with the axis of angled central lumen 2112 when distractor 2100 has been affixed to holder 2400. This arrangement permits for distractor 2100 to be held in place in the intra-articular facet joint, while driver 2430 is used to drive screw 2432 (or other connector) through one of the two holes drilled in the vertebral facets forming the intra-articular facet joint, through angled central lumen 2112 of distractor 2100, and finally through the other of the two holes drilled in the vertebral facets forming the intra-articular facet joint. In the embodiments illustrated, driver 2430 is provided with prongs 2434 to engage with screw 2432. However, other configurations for driver 2430 would immediately suggest themselves, including chisel heads, or any one of standard screw driver configurations.

In the illustrated embodiments, the distractors are substantially symmetric in shape and configuration. However, alternatives including tapering and irregular shapes may also be preferred. Other shapes would be equally suitable provided they achieve the objective of intrafacetal distraction without causing trauma or damage to surrounding bone, tissue or nerves. Shape of the distractors may also be modified with a view to alter the curvature of the spine.

The distance separating the two abutment surfaces of the distractor may be selected to be less than or equal to the distraction sought to be achieved between the articular facets. In an embodiment this distance may be between 2 mm and 4 mm, and in a preferred embodiment is 2.5 mm. The distance between any two points on the perimeter of any one of the two abutment surfaces of the distractor may in an embodiment be less than 12 mm, in a particular embodiment is between 6 mm and 12 mm, and in a preferred embodiment is 8 mm.

Material for the distractor may comprise medical grade titanium, polyether-ether-ketone (PEEK), poly(methylmethacrylate) (PMMA), stainless steel, or any other biologically inert material with the desired rigidity. Medical grade titanium provides a preferred material for reasons of magnetic resonance imaging (MRI) compatibility combined with mechanical strength.

In several of the illustrated embodiments of holders for the impactor, the holder is discussed comprising an inner cylindrical body nested within an outer cylindrical sleeve. It would be immediately apparent that other embodiments are possible, including having a single solid body instead of the nested arrangement shown.

In an embodiment of the method invention involving treatment of cervical spondylosis, a patient may be placed prone with the head-end of the operating table raised at an elevation of 30 degrees. Gardner-Wells traction is thereafter applied with the objective of stabilizing the head during surgery. The direction of traction results in a near floating head position and avoids pressure on the face. A midline skin incision may thereafter be made and the spinous process exposed to identify the exact level of surgery. Thereafter the facets on both sides of the relevant spinal segment may be exposed following a subperiosteal dissection. The physical appearance of the articular facets may then be evaluated, and facets having excessive movements and near open joint cavities may be examined for instability. In cases where there is evidence of joint instability on inspection, facetal fixation may be favorably considered despite marginal evidence of cord compression opposite the disc space.

The device of the present invention to be implanted in the articular cavity requires the facets corresponding to said cavity to be first distracted. The facets may be distracted using osteotomes of appropriate sizes. The flat end of an osteotome may be introduced into the facet joint and then rotated sufficiently (somewhere between 0 and 90 degrees) to effect appropriate distraction of the facets. Articular cartilage may thereafter be widely removed using the screwing motion of the osteotome and if necessary, a power drill. Removal of the articular cartilage helps in early bone fusion. The device is then affixed to an impactor and maneuvered (or if necessary impacted using gentle hammering) into the joint. The impactor holds the device firmly by virtue of its connectors and simultaneously restrains the device from traversing beyond the confines of the articular joint.

In an embodiment of the invention, the inter-spinous and inter-laminar ligaments may be widely removed (i.e. may be removed in entirety or substantially removed along their entire extent) in the treated spinal segments. This removal assists in avoiding any further movement of the region that ultimately has to undergo bone fusion. Bone graft may thereafter be harvested from the iliac crest or other appropriate area and placed over adequately prepared host bone area of the laminae and spinous process to aid arthrodesis. For operations on lumbar sponsylosis, the patient is prone and positioned to obliterate the lumbar curvature. Rest of the operative procedure is the same. Spinous process of the lumbar vertebra is sectioned at its base and shredded into small pieces and is used as bone graft.

I claim:

1. A combined assembly of a vertebral facet distractor and a holder, the combined assembly comprising:
    a vertebral facet distractor having first and second abutment surfaces separated by a predetermined distance, the vertebral facet distractor having a central lumen extending between the first and second abutment surfaces at an angle with respect to the first and second abutment surfaces; and
    a holder including:
        (1) an outer sleeve having a first end and a second end;
        (2) an inner body extending through the outer sleeve and having a head portion located adjacent to the first end of the outer sleeve and a tip located adjacent to the second end of the outer sleeve and engaged with the vertebral facet distractor; and
        (3) an angled arm including:
            (a) a first arm section having a first end that is affixed to the first end of the outer sleeve and a second end; and
            (b) a second arm section including a sleeve that is capable of interchangeably housing a drill or a driver, the sleeve having an end that is affixed at an angle to the second end of the first arm section such that either of a drill or driver housed within the sleeve traverses a path coincident with the angled central lumen of the vertebral facet distractor.

2. The combined assembly as claimed in claim 1, wherein the vertebral facet distractor includes an opening, and wherein the tip of the inner body engages the opening.

3. The combined assembly as claimed in claim 1, wherein the first arm section and the second arm section are adjustably connected so as to enable variation of an angle therebetween.

4. The combined assembly as claimed in claim 1, wherein an angle between the first arm section and the second arm section is substantially the same as the angle of the central lumen.

\* \* \* \* \*